US012036282B2

(12) United States Patent
Goldys et al.

(10) Patent No.: US 12,036,282 B2
(45) Date of Patent: Jul. 16, 2024

(54) LIPOSOMAL SYSTEM FOR DRUG DELIVERY

(71) Applicant: NewSouth Innovations PTY Limited, Sydney (AU)

(72) Inventors: Ewa Goldys, Kingsford (AU); Wei Deng, Carlingford (AU)

(73) Assignee: NewSouth Innovations Pty Limited, New South Wales (AU)

(*) Notice: Subject to any disclaimer, the term of this patent is extended or adjusted under 35 U.S.C. 154(b) by 348 days.

(21) Appl. No.: 16/770,930

(22) PCT Filed: Dec. 6, 2018

(86) PCT No.: PCT/AU2018/000247
§ 371 (c)(1),
(2) Date: Jun. 8, 2020

(87) PCT Pub. No.: WO2019/109126
PCT Pub. Date: Jun. 13, 2019

(65) Prior Publication Data
US 2020/0330599 A1    Oct. 22, 2020

(30) Foreign Application Priority Data

Dec. 6, 2017 (AU) ................. 2017904916

(51) Int. Cl.
*A61K 41/00* (2020.01)
*A61K 9/00* (2006.01)
(Continued)

(52) U.S. Cl.
CPC ........ *A61K 41/0071* (2013.01); *A61K 9/0009* (2013.01); *A61K 9/1271* (2013.01);
(Continued)

(58) Field of Classification Search
CPC ..... A61K 9/127; A61K 9/1271; A61K 9/1272
See application file for complete search history.

(56) References Cited

U.S. PATENT DOCUMENTS 5,820,879 A    10/1998  Fernandez et al.
2004/0010218 A1*  1/2004  Henderson ............. A61P 43/00
                                                              604/6.08
(Continued)

FOREIGN PATENT DOCUMENTS

CN    104645331 A  *  5/2015
CN    105288646 A  *  2/2016
(Continued)

OTHER PUBLICATIONS

Anu Puri. "Phototriggerable Liposomes: Current Research and Future Perspectives." Pharmaceutics, vol. 6, 2014, pp. 1-25. (Year: 2014).*

(Continued)

*Primary Examiner* — Isaac Shomer
(74) *Attorney, Agent, or Firm* — Myers Bigel, P.A.

(57) ABSTRACT

A liposomal system for delivery of an active agent comprising: lipid component forming a liposome; destabilizing agent associated with the lipid component, the destabilizing agent capable of forming reactive oxygen species to oxidise unsaturated lipids and destabilise liposomal membrane; and an active agent; wherein the active agent is releasable from the liposome by exposure to high energy electromagnetic radiation.

16 Claims, 10 Drawing Sheets

Specification includes a Sequence Listing.

(51) Int. Cl.

| | |
|---|---|
| A61K 9/127 | (2006.01) |
| A61K 31/519 | (2006.01) |
| A61K 31/704 | (2006.01) |
| A61K 31/7048 | (2006.01) |
| A61K 33/242 | (2019.01) |
| A61K 47/69 | (2017.01) |
| A61K 49/00 | (2006.01) |
| A61N 5/10 | (2006.01) |
| C12N 15/113 | (2010.01) |

(52) U.S. Cl.
CPC .......... *A61K 9/1272* (2013.01); *A61K 31/519* (2013.01); *A61K 31/704* (2013.01); *A61K 31/7048* (2013.01); *A61K 33/242* (2019.01); *A61K 47/6911* (2017.08); *A61K 49/0021* (2013.01); *A61K 49/0084* (2013.01); *A61N 5/10* (2013.01); *C12N 15/113* (2013.01); *A61N 2005/1098* (2013.01); *C12N 2310/11* (2013.01); *C12N 2320/32* (2013.01); *C12N 2320/35* (2013.01)

(56) References Cited

U.S. PATENT DOCUMENTS

| | | | |
|---|---|---|---|
| 2011/0238001 | A1 | 9/2011 | Chen et al. |
| 2012/0041357 | A1* | 2/2012 | Fologea .................. A61K 9/127 424/9.1 |
| 2014/0255472 | A1* | 9/2014 | Geall .................... A61K 9/1271 514/44 R |
| 2016/0136289 | A1* | 5/2016 | Puri ...................... A61K 9/0019 604/20 |
| 2017/0252466 | A1 | 9/2017 | Peyman |

FOREIGN PATENT DOCUMENTS

| | | | |
|---|---|---|---|
| WO | 2009038776 | A1 | 3/2009 |
| WO | 2009105662 | A1 | 8/2009 |
| WO | 2013070872 | A1 | 5/2013 |
| WO | 2016191556 | A1 | 12/2016 |
| WO | WO-2017201528 | A1 * | 11/2017 ........... A61K 31/136 |

OTHER PUBLICATIONS

Nikolai Gross et al. "Choroidal neovascularization reduced by targeted drug delivery with cationic liposome-encapsulated paclitaxel or targeted photodynamic therapy with verteporfin encapsulated in cationic liposomes." Molecular Vision, vol. 19, 2013, pp. 54-61. (Year: 2013).*

Zofia Kautzka et al. "Light-triggered liposomal cargo delivery platform incorporating photosensitizers and gold nanoparticles for enhanced singlet oxygen generation and increased cytotoxicity." International Journal of Nanomedicine, vol. 12, Feb. 2, 2017, pp. 969-977. (Year: 2017).*

Joshua Grimes. "Patient-Specific Internal Dose Calculation Techniques for Clinical Use in Targeted Radionuclide Therapy." PhD Thesis, The University of Guleph, 2013, pp. i-xxii and 1-164. (Year: 2013).*

Linlin Zhao et al. "Enhanced cellular uptake and phototoxicity of Verteporfin-conjugated gold nanoparticles as theranostic nanocarriers for targeted photodynamic therapy and imaging of cancers." Materials Science and Engineering C, vol. 67, 2016, pp. 611-622. (Year: 2016).*

Muhammad Kashif Riaz et al. "Surface Functionalization and Targeting Strategies of Liposomes in Solid Tumor Therapy: A Review. " International Journal of Molecular Science, vol. 19(195), 2018, pp. 1-27. (Year: 2018).*

Rongrong Wang et al. "Application of poly(ethylene glycol)-distearoylphosphatidylethanolamine (PEG-DSPE) block copolymers and their derivatives as nanomaterials in drug delivery." International Journal of Nanomedicine, 2012, vol. 7, pp. 4185-4198 (Year: 2012).*

Xiamin Cheng et al. "Liposomes as Multifunctional Nano-Carriers for Medicinal Natural Products." Frontiers in Chemistry, vol. 10, Aug. 2022, pp. 1-20. (Year: 2022).*

Yifei Huang et al. "A Novel Hydrolysis-Resistant Lipophilic Folate Derivatives Enables Stable Delivery of Targeted Liposomes in Vivo." International Journal of Nanomedicine, vol. 9, 2014, pp. 4581-4595. (Year: 2014).*

Clarivate Analytics. English Translation of CN 105288646 A. Originally published in Chinese on Feb. 3, 2023, obtained by examiner on Dec. 7, 2023, pp. 1-17. (Year: 2017).*

Danielle Irby, Chengan Du, and Feng Li. "Lipid-Drug Conjugate for Enhancing Drug Delivery." Molecular Pharmaceutics, vol. 14, 2017, pp. 1325-1338, published Jan. 12, 2017. (Year: 2017).*

Sarah J. Leung and Marek Romanowski. "Light-Activated Content Release from Liposomes." Theranostics, vol. 2(10), 2012, pp. 1020-1036. (Year: 2012).*

Clarivate Analytics. English Translation of CN 104645331 A. Obtained by examiner on Mar. 21, 2024. Originally published in Chinese on May 27, 2015. (Year: 2015).*

"Extended European Search Report corresponding to European Application No. 18885426.9 dated Jul. 23, 2021".

"International Preliminary Report on Patentability corresponding International Application No. PCT/AU2018/000247 Issued Jun. 9, 2020".

"Office Action corresponding to Chinese Application No. 201880088777.4 issued Jan. 27, 2022".

"Office Action corresponding to Chinese Application No. 201880088777.4 issued Jul. 21, 2022".

Clement, Sandhya , et al., "Nanoparticle-mediated singlet oxygen generation from photosensitizers", Journal of Photochemistry and Photobiology A: Chemistry 332:66-71 (2017).

Clement, Sandhya , et al., "Verteprofin conjugated to gold nanoparticles for fluorescent cellular bioimaging and X-ray mediated photodynamic therapy", Microchimica Acta 184,:1765-1771 (Mar. 22, 2017).

Clement, Sandhya , et al., "X-ray induced singlet oxygen generation by nanoparticlephotosensitizer conjugates for photodynamic therapy: determination of singlet oxygen quantum yield", Scientific Reports 6:1-9 (Jan. 28, 2016).

Dicheva, Bilyana M, et al., "Targeted and heat-triggered doxorubicin delivery to tumors by dual targeted cationic thermosensitive liposomes", Journal of Controlled Release 195:37-48 (Aug. 29, 2014).

Ferreira, Diego Dos Santos , et al., "pH-sensitive liposomes for drug delivery in cancer treatment", Therapeutic delivery 4(9):1099-1123 (2013).

Ichikawa, Kanae , et al., "Antiangiogenic photodynamic therapy (PDT) using Visudyne causes effective suppression of tumor growth", Cancer Letters 205:39-48 (2004).

Garashi, Akira , et al., "Liposomal photofrin enhances therapeutic efficacy of photodynamic therapy against the human gastric cancer", Toxicology Letters 145:133-141 (May 12, 2003).

Klein, Stefanie , et al., "Oxidized silicon nanoparticles for radiosensitization of cancer and tissue cells", Biochemical and Biophysical Research Communications 434(2):217-222 (Mar. 25, 2013).

Kono, Kenji , et al., "Highly temperature-sensitive liposomes based on a thermosensitive block copolymer for tumor-specific chemotherapy", Biomaterials 31:7096-7105 (Jun. 30, 2010).

Leung, Sarah J, et al., "Light-Activated Content Release from Liposomes", Theranostics 2(10): 1020-1036 (Oct. 18, 2012).

Meng, Fan-Xu , et al., "Preliminary Studies on X-Ray-sensitive Liposome", Chemical Research in Chinese Universities 28(2):319-322 (2012).

Miranda, Dyego , et al., "Mechanisms of light-induced liposome permeabilization", Bioengineering & Translational Medicine 1:267-276 (Aug. 29, 2016).

Nahire, Rahul , et al., "pH-Triggered Echogenicity and Contents Release from Liposomes", Molecular pharmaceutics 11:4059-4068 (Oct. 1, 2014).

Rwei, Alina Y, et al., "Enhanced Triggering of Local Anesthetic Particles by Photosensitization and Photothermal Effect Using a Common Wavelength", Nano Letters 17:7138-7145 (Oct. 23, 2017).

(56) References Cited

OTHER PUBLICATIONS

Yue, Caixia, et al., "Mitochondria-targeting near-infrared lighttriggered thermosensitive liposomes for localized photothermal and photodynamic ablation of tumors combined with chemotherapy", Nanoscale 9:11103-11118 (Jun. 22, 2017).

Zhao, Linlin, et al., "Enhanced cellular uptake and phototoxicity of Verteporfin-conjugated gold nanoparticles as theranostic nanocarriers for targeted photodynamic therapy and imaging of cancers", Materials Science and Engineering: C 67:611-622 (Oct. 1, 2016).

Zhou, Fangyuan, et al., "Theranostic Prodrug Vesicles for Reactive Oxygen Species—Triggered Ultrafast Drug Release and Local-Regional Therapy of Metastatic Triple-Negative Breast Cancer", Advanced Functional Materials 27:1-12 (2017).

\* cited by examiner

LIPOSOMAL SYSTEM FOR DRUG DELIVERY

This is a U.S. National Stage of International Application PCT/AU2018/000247, filed Dec. 6, 2018.

STATEMENT OF PRIORITY

This application is a 35 U.S.C. § 371 national phase application of PCT/AU2018/00247, filed Dec. 6, 2018, which claims priority from Australian Application No. 2017904916, filed Dec. 6, 2017, the entire contents of each of which are incorporated by reference herein.

STATEMENT REGARDING ELECTRONIC FILING OF A SEQUENCE LISTING

A Sequence Listing in text format, submitted under 37 C.F.R. § 1.831-1.834, entitled 9875-45 ST25, 639 bytes in size, generated on Nov. 11, 2022, and filed electronically, is provided in lieu of a paper copy. This Sequence Listing is hereby incorporated by reference into the specification for its disclosures.

TECHNICAL FIELD

The technology relates to drug delivery systems using liposomes.

RELATED APPLICATION

This application is based on and claims priority to Australian provisional patent application No 2017904916 filed on 6 Dec. 2017, the content of which is incorporated by reference in its entirety.

BACKGROUND

The development and application of various nanomaterial designs for gene and drug delivery is currently one of the key focus areas in nanomedicine. Although viral carriers have been traditionally used as a gene/drug delivery method (Thomas et al 2003; Zhang et al 2012), its application is hindered by a range of limitations including toxin production, limited size of loaded materials, packaging difficulties and the risk of recombination (Luo, D. & Saltzman 2000). To overcome these limitations, synthetic nanomaterial-based systems have been extensively studied and developed. Among these nanomaterials, liposomes have been well established as an effective drug delivery system, due to the simplicity of their preparation and unique characteristics. Liposomes consist of an aqueous core surrounded by a lipid bilayer similar to cell membranes, which facilitates cellular uptake of liposomes. The lipids forming liposomes are amphipathic, thus allowing the encapsulation of both hydrophobic and hydrophilic molecules as well as colloidal particles. Liposomes are usually biocompatible and biodegradable, which makes them suitable for clinical applications. Conventional liposomes, for example, commercial lipofectamine 2000, cannot achieve the on-demand content release, which limits their therapeutic applications, although they have the high delivery efficiency.

Conventional liposomes gradually release the encapsulated cargos in an uncontrollable manner, which limits their therapeutic efficacy. In contrast, triggerable liposomes are able to release genes/drugs in a more controlled manner, usually much faster and, depending on triggering modality, also to a specific area, and these properties contribute to their potentially greater clinical success. Several strategies have been previously employed to design responsive liposomes whose bilayer could be destabilized by using physiological and external stimuli. The triggering approaches previously reported include changes in pH (typical in cancer) (Nahire et al, 2014; Ferreira et al, 2013), externally delivered heat, for example via alternating magnetic field or infrared light (Dicheva et al, 2014; Kono et al, 2010), enzymes (Sarkar et al, 2005; Arouriet al, 2015) and non-thermal effects caused by light irradiation (Leung et al, 2012; Puri, 2013). These approaches have certain limitations, in particular visible light triggering of light-sensitive liposomes is limited by the relatively shallow (few mm) penetration of light into biological tissues (Wilson, and Patterson, 2008). As a result of this shallow penetration depth, visible light cannot activate photosensitizers (PS) located deeply in the body and generate sufficient amount of singlet oxygen ($^1O_2$) or other reactive oxygen species (ROS) to release the liposome cargo required for the therapeutic effects.

The present inventors have developed a liposomal system suitable for delivering a drug or biologically active agent to a subject.

SUMMARY

In a first aspect, there is provided a liposomal system for delivery of an active agent, the system comprising:
lipid component forming a liposome;
destabilizing agent associated with the lipid component, the destabilizing agent capable of forming reactive oxygen species to oxidise unsaturated lipids and destabilise liposomal membranes; and
an active agent in the liposome;
wherein the active agent is releasable from the liposome by exposure to high energy electromagnetic radiation.

The lipid component can include any suitable lipids that form stable liposomes. Useful liposomes are generally formed from naturally occurring lipids such as phospholipids and cholesterol. Examples of suitable lipids include 1,2-dioleoyl-sn-glycero-3-phosphocholine (DOPC) and 1,2-di-(9Z-octadecenoyl)-3-trimethylammonium-propane (DOTAP), or 1,2-dioleoyl-sn-glycero-3-phosphoethanolamine (DOPE) and N-[1-(2,3-dioleyloxy)propyl]-N,N,N-trimethylammonium chloride (DOTMA).

In an embodiment the lipid component is formed from DOPC and DOTAP. DOPC can load highly hydrophobic molecules and DOTAP can facilitate cellular uptake due to its positive charge.

In an embodiment the destabilizing agent is a nanoparticle. The nanoparticle can be a metal nanoparticle or an inorganic nanoparticle. The metal nanoparticle can be selected from gold, silver and bismuth.

In an embodiment the metal nanoparticle is a gold nanoparticle.

In an embodiment the inorganic nanoparticle can be cerium fluoride ($CeF_3$).

In an embodiment the destabilizing agent is a photosensitizer. Suitable photosensitizers include verteporfin (VP), rose bengal, aminolevulinic acid and photofrin. It will be appreciated that other photosensitizers can be used in the present technology.

In an embodiment the destabilizing agent is a nanoparticle and a photosensitizer.

The destabilizing agent can be a combination of gold nanoparticles and verteporfin.

In an embodiment the reactive oxygen species is $^1O_2$ (singlet oxygen being a high energy form of oxygen).

In an embodiment the active agent is a chemotherapy agent, pharmaceutical, medical imaging agent, antisense oligonucleotide and small interfering RNA (siRNA) molecule for gene silencing and therapy, biologically active agent, antibody, antibody fragment, protein peptide, or nucleic acid.

In an embodiment the chemotherapy agent is doxorubicin, vincristine, 5-fluorouracil, or etoposide phosphate (Etopophos). It will be appreciated, however, that the present technology is suitably for other agents suitable formulated for the liposome.

In an embodiment the chemotherapy agent is doxorubicin.

In an embodiment the active agent is an antisense oligonucleotide.

The liposomes may further comprise a material to cause uptake of the liposomes into a target region or target cells of a subject. The material may be an antigen, antibody, antibody fragment, peptide, hormone, cytokine, folate, ligand and receptor. For example, liposome-folate conjugates have been used to make liposomes tumour cell-specific due to folate receptor overexpressed on many cancer cells. These folate-conjugated liposomes will be able to target cancer cells and deliver their cargo intracellularly through receptor-mediated endocytosis.

In an embodiment the high energy electromagnetic radiation is x-ray radiation or gamma-ray radiation. Exposure of the liposome to high energy electromagnetic radiation such as x-rays causes generation of $^1O_2$ in the lipid components to destabilise the liposomes leading to the release of the active agent. The generation of $^1O_2$ can come from a photosensitizer or nanoparticle in the liposome.

In an embodiment the high energy electromagnetic radiation has an energy of at least about 6 MeV.

In a second aspect there is provided a liposomal system for delivery of an active agent, the system comprising:
  lipid component comprising 1,2-dioleoyl-sn-glycero-3-phosphocholine (DOPC) and 1, 2-di-(9Z-octadecenoyl)-3-trimethylammonium-propane (DOTAP), or 1,2-dioleoyl-sn-glycero-3-phosphoethanolamine (DOPE) and N-[1-(2,3-dioleyloxy)propyl]-N,N,N-trimethylammonium chloride (DOTMA) forming a liposome;
  destabilizing agent comprising a nanoparticle, a photosensitizer, or nanoparticle and a photosensitizer associated with the lipid component, the destabilizing agent capable of forming reactive oxygen species to oxidise unsaturated lipids and destabilise liposomal membranes; and
  an active agent selected from a chemotherapy agent or an antisense oligonucleotide in the liposome;
  wherein the active agent is releasable from the liposome by exposure to high energy electromagnetic radiation.

In a third aspect there is provided a method for administering an active agent to a subject, the method comprising:
  providing a liposomal system according to the first or second aspect to a subject; and
  exposing the subject to high energy electromagnetic radiation to release the active agent from the liposome to treat the subject.

The liposomal system can be provided to the subject by any suitable route such as oral, intravenous topical, and enteral.

The method may further comprise allowing the liposomes to be taken up by cells in a site of the subject prior to exposing the subject to high energy electromagnetic radiation. The site maybe a tumour, infection, wound, organ or its region such as bone region, skin, and blood vessels, including in the eye.

The high energy electromagnetic radiation can be provided by exposing the patient to x-rays or gamma-ray radiation. The high energy electromagnetic radiation can be site directed or whole subject exposure.

In a fourth aspect there is provided use of a liposomal system according to the first or second aspect to administer an active agent to a subject.

In a fourth aspect there is provided use of a liposomal system according to the first or second aspect in the manufacture of a medicament to administer an active agent to a subject.

The subject may be any animal such as a human.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

In order that the present technology may be more clearly understood, preferred embodiments will be described with reference to the following drawings and examples.

DEFINITIONS

Figure 1:
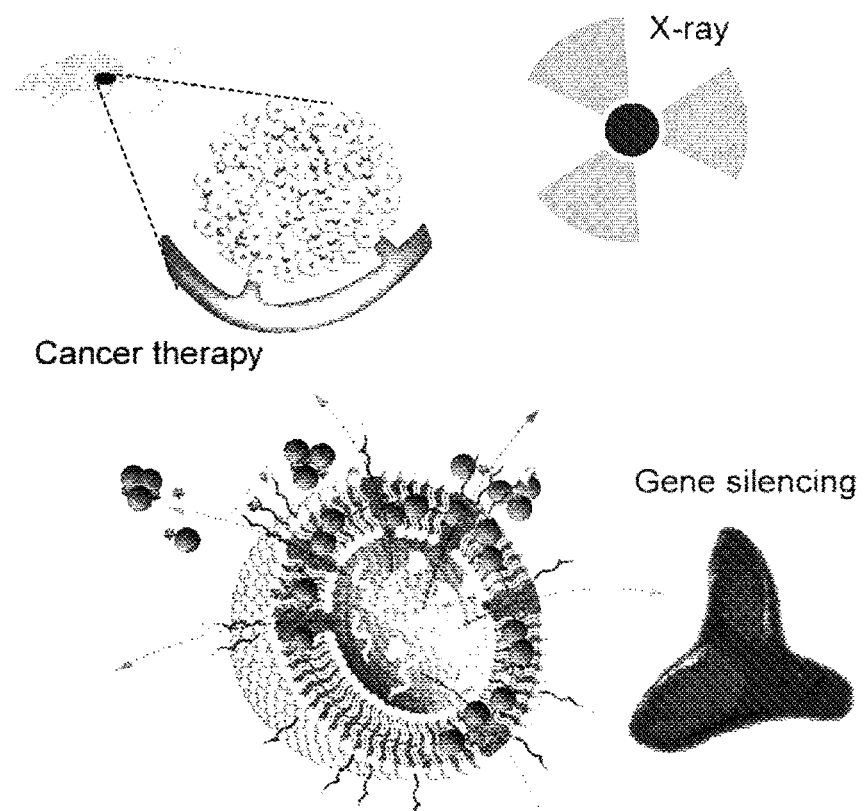
FIG. 1 is a schematic illustration of gene silencing and cancer cell-killing effect of a liposomal delivery platform incorporating verteporfin and gold nanoparticles triggered by X-ray radiation. Two types of cargos, antisense oligonucleotide and Doxorubicin (Dox), were respectively entrapped inside a liposomal middle cavity for demonstration of in vitro gene and drug delivery. In vivo demonstration was also conducted by using liposomes incorporating Dox and triggered by X-ray.

Throughout this specification, unless the context clearly requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, the term 'consisting of' means consisting only of.

Any discussion of documents, acts, materials, devices, articles or the like which has been included in the present specification is solely for the purpose of providing a context for the present technology. It is not to be taken as an admission that any or all of these matters form part of the prior art base or were common general knowledge in the field relevant to the present technology as it existed before the priority date of each claim of this specification.

Unless the context requires otherwise or specifically stated to the contrary, integers, steps, or elements of the technology recited herein as singular integers, steps or elements clearly encompass both singular and plural forms of the recited integers, steps or elements.

In the context of the present specification the terms 'a' and 'an' are used to refer to one or more than one (ie, at least one) of the grammatical object of the article. By way of example, reference to 'an element' means one element, or more than one element.

In the context of the present specification the term 'about' means that reference to a figure or value is not to be taken as an absolute figure or value, but includes margins of variation above or below the figure or value in line with what a skilled person would understand according to the art, including within typical margins of error or instrument limitation. In other words, use of the term 'about' is understood to refer to a range or approximation that a person or skilled in the art would consider to be equivalent to a recited value in the context of achieving the same function or result.

Those skilled in the art will appreciate that the technology described herein is susceptible to variations and modifications other than those specifically described. It is to be understood that the technology includes all such variations and modifications. For the avoidance of doubt, the technology also includes all of the steps, features, and compounds referred to or indicated in this specification, individually or collectively, and any and all combinations of any two or more of said steps, features and compounds.

DESCRIPTION OF EMBODIMENTS

The present inventors have designed triggered liposomes by co-embedding photosensitizers and/or gold nanoparticles (3-5 nm) inside a lipid bilayer. Gold was chosen in this work as, due to its high atomic number it strongly interacts with X-ray radiation as shown, for example, by gold nanoparticle-induced radiation enhancement inside biological tissue. Although in the design the photosensitisers can be the primary source of reactive oxygen species (ROS) to oxidise unsaturated lipids and destabilise liposomal membranes, gold nanoparticles exposed to X-rays also generate some level of ROS. More complex effects are also possible, for example secondary electrons produced during the interaction of X-rays with gold nanoparticles may transfer from gold to a photosensitizer and lead to PS-induced generation of $^1O_2$ (singlet oxygen is a high energy form of oxygen) or other ROS. As a photosensitizer verteporfin (VP) was chosen to demonstrate the technology, clinically approved for photodynamic therapy (PDT) of age-related macular degeneration. 1,2-dioleoyl-sn-glycero-3-phosphocholine (DOPC) and 1, 2-di-(9Z-octadecenoyl)-3-trimethylammonium-propane (DOTAP) were chosen as lipid components in the liposome formulation because DOPC can load highly hydrophobic molecules and DOTAP can facilitate cellular uptake due to its positive charge. The $^1O_2$ generation from different liposome samples and destabilization of the lipid bilayer by $^1O_2$ under 365 nm LED illumination with different time points (2, 4, 6, 8 and 10 min) and X-ray radiation with different dosage (1, 2 and 4 Gy) were assessed by using the Singlet Oxygen Green Sensor (SOSG) and calcein release assays, respectively. SOSG is a commonly used and highly specific fluorescence probe for the detection of $^1O_2$ generation. It was identified to be fluorescein covalently bound with an anthracene moiety. Calcein is a fluorescent dye that self-quenches at high concentration which makes it possible to detect its release from the liposomes to the surrounding environment by monitoring the increase in calcein fluorescence intensity upon X-ray radiation. Additionally, $^1O_2$ quantum yield under UV light illumination and the number of $^1O_2$ generated as a result of X-ray radiation were also calculated based on experimental data using the methodology previously developed by the inventors.

Triggered release of the liposome cargo by X-rays was verified by (a) demonstrating the efficiency of X-ray triggered gene knockdown and (b) the increased effectiveness of chemotherapy based on this liposomal delivery system (FIG. 1). For gene silencing, antisense oligonucleotides complementary to a specific pituitary adenylate cyclase-activating polypeptide (PACAP) receptor, PAC1R, were encapsulated inside the liposomes. Following the liposome take-up by rat PC12 cells, the X-ray radiation at a dose of 4 Gy was applied. As a result of exposure to ionising radiation, the $^1O_2$ generated in a lipid bilayer destabilised the liposomes, leading to the release of antisense oligonucleotides. This antisense nucleotide was then able to prevent the translation of the PAC1R mRNA by blocking the translation initiation complex. Gene knockdown was monitored by observing a decrease in the fluorescence intensity from indirect immunofluorescence staining of PAC1R in cells after X-ray irradiation. For X-ray triggered chemotherapy, an antitumour drug, doxorubicin (Dox), was loaded into the liposomes. The liposomes were taken up by human colorectal cancer HCT116 cells and X-rays applied. The in vitro cancer cell-killing efficacy of liposome-formulated Dox was subsequently examined by the MTS assays. For comparison, control experiments were also conducted at the same experimental conditions apart from the omission of X-ray radiation.

X-ray triggerable liposomes were developed by introducing gold nanoparticles and photosensitizer verteporfin inside the liposomal bilayer. The singlet oxygen generation quantum yield was quantified for 6 MeV X-ray radiation where the dose of 4 Gy was found to generate about 7250 singlet oxygen molecules per liposome. The singlet oxygen molecules destabilise the liposomal membrane, causing the release of cargos (gene silencing agents and/or drugs) from the liposomal cavity. This is demonstrated by X-ray triggered gene knockdown of one of the pituitary adenylate cyclase-activating polypeptide (PACAP) receptors, PAC1R, in rat PC12 cells. The same X-ray triggered liposomes loaded with a chemotherapy drug, doxorubicin killed human colorectal cancer HCT116 cells more effectively than in the absence of X-ray triggering. This indicates the possibility of a synergistic effect in the course of standard radiotherapy with 6 MeV X-rays combined with chemotherapy delivered via X-ray triggered liposomes. Importantly, the X-ray mediated liposome release strategy offers new prospects for deep tissue photodynamic therapy, by removing its depth limitation. The new type of liposomes combined with radio-, chemo- or gene therapies may therefore offer new cancer treatment options.

Materials
Liposomes

The lipid component can include any suitable lipids that form stable liposomes. Useful liposomes are generally formed from naturally occurring lipids such as phospholipids and cholesterol (Miranda and Lovell, 2016).

Liposomes are generally formed by the self-assembly of dissolved lipid molecules, each of which contains a hydrophilic head group and hydrophobic tails. These lipids take on associations which yield entropically favorable states of low free energy, in some cases forming bimolecular lipid leaflets. Such leaflets are characterized by hydrophobic hydrocarbon tails facing each other and hydrophilic head groups facing outward to associate with aqueous solution. At this point, the bilayer formation is still energetically unfavorable because the hydrophobic parts of the molecules are still in contact with water, a problem that is overcome through curvature of the forming bilayer membrane upon itself to form a vesicle with closed edges. This free-energy-driven self-assembly is stable and has been exploited as a powerful mechanism for engineering liposomes specifically to the needs of a given system. Lipid molecules used in liposomes are conserved entities with a head group and hydrophobic hydrocarbon tails connected via a backbone linker such as glycerol. Cationic lipids commonly attain a positive charge through one or more amines present in the polar head group. The presence of positively charged amines facilitates binding with anions such as those found in DNA. The liposome thus formed is a result of energetic contributions by Van der Waals forces and electrostatic binding to the DNA which partially dictates liposome shapes. Because of the polyanionic nature of DNA, cationic (and neutral) lipids are typically used for gene delivery, while the use of anionic liposomes has been fairly restricted to the delivery of other therapeutic macromolecules (Balazs and Godbey, 2011).

Well-characterized and widely used commercial reagents for cationic lipid transfection include N-[1-(2,3-dioleyloxy) propyl]-N,N,N-trimethylammonium chloride(DOTMA), [1,2-bis(oleoyloxy)-3-(trimethylammonio)propane] (DOTAP), 3β[N—(N', N'-dimethylaminoethane)-carbamoyl] cholesterol (DC-Chol), and dioctadecylamidoglycylspermine (DOGS). Dioleoylphosphatidylethanolamine (DOPE), a neutral lipid, can be used in conjunction with cationic lipids because of its membrane destabilizing effects at low pH, which aide in endolysosomal escape.

The lipid bilayer can include any suitable lipids that form stable liposomes. Examples of suitable lipids include 1,2-dioleoyl-sn-glycero-3-phosphocholine (DOPC) and 1, 2-di-(9Z-octadecenoyl)-3-trimethylammonium-propane (DOTAP), or 1,2-dioleoyl-sn-glycero-3-phosphoethanolamine (DOPE) and N-[1-(2,3-dioleyloxy)propyl]-N,N,N-trimethylammonium chloride (DOTMA).

A lipid bilayer formed from DOPC and DOTAP is suitable for use as liposomes for the present technology. DOPC can load highly hydrophobic molecules and DOTAP can facilitate cellular uptake due to its positive charge. Similar to combination of DOPC and DOTAP, DOTMA can be coupled with DOPE in a 1/1 molar ratio to form liposomes where cationic DOTMA can enhance cellular uptake and DOPE has membrane destabilizing effects with external triggering (Farhood, 1995).

Destabilizing Agents
Nanoparticles

The nanoparticles can be metal nanoparticles or inorganic nanoparticles. Suitable metal nanoparticles include gold, silver and bismuth that can enhance X- or gamma-ray radiation and energy transfer from X-ray or gamma-ray radiation (Su et al, 2014).

The inorganic nanoparticle can be selected from cerium fluoride (CeF$_3$). The inorganic nanoparticle can be used as an efficient scintillator that produces visible light to trigger ROS generation upon X-ray or gamma-ray excitation (Clement et al, 2016).

Photosensitizers

Suitable photosensitizers include verteporfin (VP), rose bengal, aminolevulinic acid and photofrin. VP (trade name Visudyne) is a benzoporphyrin derivative that is traditionally used as a photosensitizer for photodynamic therapy to eliminate the abnormal blood vessels in the eye associated with conditions such as the wet form of macular degeneration.

A combination of nanoparticles and photosensitizers is also useful for the present technology. For example, gold nanoparticles and VP have been shown to work well in the examples below.

Active Agents

The active agent can be any suitable agent that can be incorporated into a liposome. The active agent can be a chemotherapy agent, pharmaceutical, medical imaging agents, antisense oligonucleotides and small interfering RNA (siRNA) molecules for gene silencing and therapy, biologically active agent, antibody, antibody fragment, protein peptide, or nucleic acid.

In an embodiment the chemotherapy agent is doxorubicin, vincristine, 5-fluorouracil, or etoposide phosphate (Etopophos). It will be appreciated, however, that the present technology is suitable for other agents suitably formulated for the liposome.

In an embodiment the chemotherapy agent is doxorubicin.

The active agent can an antisense oligonucleotide.

Doxorubicin and the antisense oligonucleotide

High Energy Electromagnetic Radiation

High energy electromagnetic radiation can be used. Electromagnetic radiation with energy higher than about 5 keV, in particular X-ray or gamma-ray radiation at an energy of at least about 6 MeV is useful for the present technology.

Liposome Uptake Material

The liposomes may further comprise a material to cause uptake of the liposomes into a target region or target cells of a subject. The material may be an antigen, antibody, antibody fragment, peptide, hormone, cytokine, ligand and receptor. For example, liposome-folate conjugates have been used to make liposomes tumour cell-specific due to folate receptor overexpressed on many cancer cells (Low et al, 2007). The conjugation can be synthesized using the following method (Gabizon et al, 1999). Briefly, excessive folic acid was dissolved in dimethyl sulfoxide. PEGylated liposomes and pyridine were added to the folic acid followed by dicyclohexylcarbodiimide. Reaction was continued at room temperature for 4 hours, followed by removing pyridine from the reaction mixture under rotary evaporation. After adding water to the mixture, it was centrifuged to remove trace insoluble materials. The supernatant was dialyzed against saline and water to remove dimethyl sulfoxide and unconjugated reactants. These folate-conjugated liposomes will be able to target cancer cells and deliver their cargo intracellularly through receptor-mediated endocytosis (Kularatne and Low, 2010).

Methods

Preparation of Liposomes Loaded with Gold Nanoparticles and Verteporfin

350 μL of DOTAP (Avanti Polar Lipids, no. 890890P) dissolved in chloroform (100 mg/mL, Sigma-Aldrich, no. 288306-1L) was mixed with 370 μL of DOPC (Avanti Polar Lipids, no. 850375P) dissolved in chloroform (100 mg/mL), followed by addition of 40 μL of gold nanoparticle suspension (Nanocomposix, Inc) and 50 μL of VP (Sigma-Aldrich, no. SML0534-5MG) dissolved in dimethyl sulfoxide (DMSO, 2.3 mg/mL, Sigma-Aldrich, no. 472301-500ML). For the synthesis of empty liposomes, liposomes containing VP alone, liposomes containing gold nanoparticles alone, other ingredients were omitted. The mixture was diluted to 1.0 mL in total volume using chloroform and vortexed gently for 10 min. Chloroform was evaporated off with a stream of Argon and the remaining DMSO was evaporated under freeze-drying, which was carried out in a freeze dryer (Alpha 1-4 LDplus, John Morris Scientific Pty Ltd). The lipid film was hydrated by adding 1.0 mL of DI water to a glass test tube, followed by vigorous stirring until the suspension was homogenized. The hydrated lipid suspension was left overnight to allow the maximal swelling of liposomes. The suspension was then extruded eleven times in an extruder (Avanti Polar Lipids, Inc) with two 1.0 mL glass syringes. The pore size of the polycarbonate membrane (Avanti Polar Lipids, Inc) was 200 nm. The resulting suspension was stored at 4° C. under argon. For encapsulation of calcein inside liposomes, 1.0 mL calcein solution (100 mM, Sigma-Aldrich, no. C0875-5G) was used as lipid hydration solution, instead of DI water. For encapsulation of oligonucleotides, 1.0 mL PBS (pH 7.4) solution containing antisense oligonucleotide (10 μM, 5'-TGGTGCTTCCCAGCCACTAT-3' (SEQ ID NO:1)) with 3' FAM labelling against PAC1R gene (Integrated DNA Technologies Pte. Ltd.) was used to hydrate lipid film, followed by the hydration procedure described above. In order to remove calcein and oligonucleotides present in the supernatant after hydration, liposomes were then centrifuged at 14000×g for 10 min by using Pall Nanosep centrifugal devices (Sigma-Aldrich) as per manufacturer's instructions.

Synthesis of Liposome-Formulated Doxorubicin (LipoDox)

The encapsulation of doxorubicin inside of liposomes was conducted as per a published protocol, using a gradient exchange method with minor modifications (Li et al, 2009). 1 mL ammonium sulphate (250 mM, Sigma-Aldrich, no. A4418-100G) was added to the glass test tube where the lipid film was produced after evaporation of organic solvent, followed by the hydration procedure described above. Free ammonium sulphate was removed by dialysis in the PBS solution (pH 7.4) with buffer exchange repeated four times. The Dox solution (10 mg/mL, Sigma-Aldrich, no. D1515-10MG) was subsequently added to hydrated liposome suspension with a drug to lipid mass ratio of 1:10, followed by incubation at 60° C. for 1 hr. Unloaded Dox was removed by dialysis in PBS solution (pH 7.4) with four time buffer exchange.

Preparation of Liposome Incorporating Etoposide (ETP), VP and Gold Nanoparticles (LipoETP)

Liposomes incorporating ETP, VP and gold nanoparticles were prepared by thin film hydration with some modifications (Sengupta et al 2000). Briefly, 100 μL of DOTAP (50 mg/mL in chloroform) was mixed with 54 μL of DOPC (100 mg/mL in chloroform), followed by addition of 6 μL of gold nanoparticle suspension, 7 μL of VP (2.3 mg/mL in DMSO) and 83.5 μL of ETP (Sigma-Aldrich, no. E1383-25MG, 1 mg/mL in chloroform and ethanol (1:1, VN)). After evaporation of organic solvent, the lipid film was hydrated with 1 mL PBS (pH 7.4). The hydration and extrusion procedure was the same as described above. The unloaded etoposide was removed by dialysis in the PBS solution (pH 7.4) with buffer exchange repeated four times.

Preparation of Folate-Conjugated Liposomes

Folate-conjugated liposomes were prepared by post-insertion of DSPE-PEG2000-Folate micelles into preformed liposomes with slight modifications (Ishida et al 1999; Yoshino et al 2012). In brief, 1 mg DSPE-PEG2000-folate (Avanti Polar Lipids, no. 880124) was dissolved in 320 µL DMSO, followed by hydration with 3.1 mL of distilled water, producing 100 µM micelle suspension. The suspension was then dialyzed three times in a 10000 MWCO dialysis tubing against 1 L water to remove DMSO. After this, 40 µL of micelles were added to 1 mL of the preformed liposome suspension in ammonium sulphate (250 mM) and heated at 60° C. for 1 hour to produce folate-tethered liposomes. Leaked ammonium sulphate and unincorporated micelles were removed by dialysis. To determine the folate content conjugated with liposomes, bare liposomes was used in conjugation procedure instead of VP-loaded liposomes. After preparation, the folate amount was determined by measuring the UV absorbance at 285 nm after lysing liposomes with 0.1% Triton X-100 and comparing with a standard curve of folic acid with the known concentration.

Characterization of Liposomes

The extinction spectra of liposomes loaded with gold nanoparticles and VP, VP alone and gold nanoparticles alone were measured using a spectrophotometer (Cary 5000 UV-Vis-NIR, Varian Inc.). Size distribution and zeta potentials of liposomes were measured with a Zetasizer Nano Series from Malvern Instruments. The morphology of liposomes was documented using Transmission Electron Microscopy (TEM). For TEM imaging, the liposome samples were prepared by placing a drop of suspension onto a copper grid and air-dried, following negative staining with one drop of 2% aqueous Uranyl Acetate for contrast enhancement. The air-dried samples were then imaged using a PHILIPS CM 10 system at an accelerating voltage of 100 KV. Images were captured with an Olympus Megaview G10 camera and iTEM software. To determine the encapsulation efficiency of oligonucleotides and Dox loaded inside of liposomes, Triton X-100 (0.1%, Sigma-Aldrich, no. T8787-50ML) was added to as-prepared liposome solution, resulting in the release of fluorescent oligonucleotide and Dox. The FAM fluorescence (Ex/Em: 494 nm/520 nm) and Dox fluorescence (Ex/Em 485/590 nm) was recorded on a Fluorolog-Tau-3 system (Jobin Yvon-Horiba, US) and compared with the corresponding oligonucleotide and Dox standard curves, respectively.

Singlet Oxygen Generation Tests with Light and X-Ray External Triggering

For light illumination, a 365 nm LED was used to illuminate the samples. 16 µL of SOSG (0.5 mM, Thermo Fisher Scientific Inc, no. S36002) was mixed with 3 mL of liposome suspension and the mixture was then placed in a cuvette, followed by illumination under a 365 nm LED (2.5 mW/cm$^2$, irradiation for 10 min). After illumination, the SOSG fluorescence at 525 nm upon 488 nm excitation was recorded using a fluorescence spectrophotometer. For X-ray radiation, a linear accelerator (6 MeV LINAC, Elekta AB, Sweden) was used to deliver different doses (1 Gy, 2 Gy and 4 Gy) to the samples. 96-well plates with 200 µL of liposome suspension and 2 µL of SOSG (0.5 mM) in each well were exposed to X-ray radiation. The irradiation of samples was carried out using 6 MeV X-ray photons from the anterior and posterior directed radiation fields. After irradiation, the SOSG fluorescence was recorded using a microplate reader (PHERAstar FS system, BMG LABTECH, Germany).

Calcein Release Assay with Light and X-Ray Irradiation

Liposomes loaded with calcein were separated from free calcein molecules by using Pall Nanosep® centrifugal devices (Sigma-Aldrich) equilibrated with 10 mM Tris/HCl. The liposomes were then activated by light illumination and ionizing radiation, respectively. The experiment process was the same as described herein, apart from the omission of SOSG. The release induced the release and subsequent dilution of the calcein previously contained in the liposomes, leading to an increase of calcein fluorescence. The calcein fluorescence signal was recorded at 510 nm upon excitation at 485 nm. The percentage of calcein release ($R_c$(%)) at various illumination time points or X-ray dosage was calculated as follows:

$$R_c(\%) = \frac{F_{t(d)} - F_0}{F_{max} - F_0} \times 100\%$$

where $F_t$ and $F_0$ respectively indicates the fluorescence intensity of calcein at various illumination time points and without illumination. $F_{max}$ refers to the total fluorescence intensity of calcein after the disruption of liposomes by adding 0.1% Triton X-100. For X-ray radiation, $F_d$ is the fluorescence intensity of calcein at various radiation doses, d.

Serum Stability of LipoDox

200 µL LipoDox was diluted in PBS (pH 7.4) containing foetal bovine serum (FBS) with different concentration (0%, 10%, 25% and 50%). All samples were dialyzed again PBS (pH 7.4) for 48 hours at 37° C. At various time points (0 h, 2 h, 4 h, 18 h, 24 h and 48 h), an aliquot of PBS was taken for the fluorescence characterisation of the released Dox. The total Dox fluorescence was measured by disrupting liposomes with 0.1% Triton X-100. The percentage of Dox release at various time points was calculated by using the same formula as that applied to the calcein release assays. In pH-triggered drug release studies, 200 µL Dox-loaded PEGylated liposome suspension was incubated with PBS (containing 10% FBS) with pH respectively adjusted to 7.4 (control), 6.0 and 5.0, followed by the same dialysis procedure and fluorescence measurement described above.

Cell Preparation and Ionizing Radiation Treatment of Cells

Rat PC12 cells, human colon adenocarcinoma cells (HCT116) and normal human colon epithelial cells (CCD 841 CoN) were purchased from the American Type Culture Collection (Rockville, MD). PC12 cells were cultured in Dulbecco's modified Eagle's medium (DMEM); HCT116 cells were cultured in McCoy's 5A (modified) medium; CCD 841 CoN cells were cultured in Eagle's Minimum Essential Medium (EMEM). All culture media were supplemented with 10% fetal bovine serum and 1% antibiotic-antimycotic. The flasks were maintained in a 37° C. incubator with 5% C02 humidified air. The cells were detached with trypsin and transferred at appropriate dilutions into 96-well plates for cell viability assays or glass-bottom petri dishes for cell imaging. For X-ray radiation experiments, the cells were radiated by using the same accelerator as described above.

Imaging and Quantitative Analysis of Cellular Uptake of Liposomes

The PC12 cells (3×10$^4$/mL) were attached to glass-bottom petri dishes and incubated at 37° C. for 24 h. After removing the culture medium, the cells were incubated with liposome suspension (25 µM) in culture medium supplemented with 10% FBS for 1 h, 4 h and 10 h. The cells were then washed with PBS (1×, PH 7.4) three times to remove free liposomes.

To assess the uptake of liposome nanoparticles, the cells were fixed with 2.5% paraformaldehyde for 10 min at room temperature, washed twice with PBS (1×, PH 7.4) and stained with Hoechst 33342 (5 µg/ml) for 10 min at room temperature before imaging. The cells were imaged using a Leica SP2 confocal laser scanning microscopy system. A violet laser at 405 nm and an argon laser at 496 nm were used for the excitation of VP and FAM-labelled oligonucleotide entrapped inside liposomes, respectively. The imaging of uptake activity of FA-targeted liposomes into HCT116 cells and CCD 841CoN cells were also conducted as mentioned above. For quantitative analysis, fluorescently labelled DOTAP (Avanti Polar Lipids, no. 810890P), was employed, instead of standard DOTAP in order to prepare fluorescent liposomes. PC12 cells ($1\times10^4$/mL) were cultured in petri dishes at 37° C. for 24 h. After removing the old culture medium, 1 mL of a fresh medium containing 10 µL of fluorescently labelled liposomes (0.5 mg/mL) was added to the petri dishes and the cells were incubated at 37° C. for a further 4 hr. After incubation, the cells were washed with fresh medium three times to remove free liposomes, detached with trypsin from the petri dishes and counted using a cell counter (Countess II FL automated cell counter from Thermo Scientific). 100 uL NaOH (1M) and 100 uL Triton X-100 (1% v/v) were subsequently added to 800 uL of cell suspension. The cells were lysed at R.T. for 2 hr with constant shaking. After cell lysis, fluorescence (Ex/Em: 460/535 nm) was recorded on a Fluorolog-Tau-3 system and compared with the standard curve of free fluorescent DOTAP solution. A detailed calculation of the number of liposomes per cell is described below Indirect Immunofluorescence Staining of PAC1R The PC12 cells were fixed with 2.5% paraformaldehyde for 10 min and permeabilized with 0.1% Triton X-100 for another 10 min at room temperature, followed by blocking with 5% bovine serum albumin for 30 min. The cells were then incubated with goat anti-PAC1R primary antibody (1:50 dilution, Santa Cruz Biotechnology, no. sc-15964) for 90 min and donkey anti goat IgG secondary antibody (1:100 dilution, Santa Cruz Biotechnology, no. sc-2024) conjugated to FITC for 30 min at room temperature.

Cytotoxicity Assays of LipoDox on HCT16 Cells after X-Ray Radiation

The in vitro anti-tumour effect of X-ray triggered LipoDox was evaluated using the MTS test. Before treatment, the HCT116 cells ($2\times10^4$/mL) were grown on 96-well plates in the culture medium with 10% FBS for 24 hr. After removing the old medium, the cells were incubated with a series of LipoDox samples diluted in the culture medium with 10% FBS for 4 hr. After incubation, the old medium was removed and a fresh medium was added to cells, followed by X-ray radiation with 4Gy. The cytotoxicity of X-ray triggered LipoDox in HCT116 cells at various time points (0 h, 2 h, 4 h and 24 h) was determined by the MTS test (Promega Co., WI, USA, no. G3582) according to manufacturer's instructions and compared with control cells without any treatment. Cell viability was then calculated as a percentage of the absorbance of the untreated control sample. The latter was set to 100%. For comparison purposes, the viability of cells treated with LipoDox alone was also evaluated in the same experimental conditions.

Toxicity of Liposomes, LipoDox and X-Ray Radiation

The PC12, HCT116 and CCD 841 CoN cells ($1-4\times10^4$/mL) were, respectively, grown on 96-well plates in a culture medium with 10% FBS for 24 hr. For liposome and LipoDox treatment experiments, the PC12 cells and CCD 841 CoN cells were, respectively, incubated with different liposome and LipoDox samples for 4 hours, followed by incubation in a fresh medium for further 24 hours. For the X-ray exposure experiments, all three types of cells were radiated with 4 Gy, followed by incubation in a fresh medium for further 24 and 48 hours. Cell viability was assessed by using the same method as described above. For X-ray treatment of pure DNA molecules and mixture of DNA and verteporfin, 50 µL of antisense oligonucleotide solution (10 µg/mL) and 50 µL of mixture solution (10 µg/mL DNA and 32 µg/mL verteporfin) was respectively exposed to X-ray radiation with different dosage (1, 2 and 4 Gy). After treatment, the gel electrophoresis was carried out in 1.2% agarose gel in Tris-acetate-EDTA (TAE) buffer at 95 V for 45 min. The gel was stained with SYBR Safe DNA Gel Stain (Thermo Fisher) and photographed under UV light using a Bio-Rad imaging system.

In Vivo Antitumour Efficacy by X-Ray Triggered Drug Release

All procedures were carried out with approval from Macquarie University Animal Ethics Committee (animal ethics approval No. 2017/001). 6-7 weeks old BALB/c nu/nu female mice (The Animal Resources Centre, Perth, Australia) were injected subcutaneously with $5\times10^6$ HCT 116 cells, suspended in McCoy's 5A (modified) medium without FBS, to the flank. Tumours were measured every two days with a caliper and volume (V) was calculated by using the following formula:

$$V = \pi/6 \times L \times W^2$$

Where L and W are the large diameter and short diameter of the tumour.

When tumour volume reached approximately 100 mm$^3$, mice were randomly divided into 4 groups (n=4 per group) for different treatments: Group A treated PBS via intratumour injection (20 µL); Group B treated with liposome suspension via intratumour injection (20 µL, 10 mg/kg); Group C treated with X-ray radiation (4 Gy, single fraction) and Group D treated with liposome suspension via intratumour injection (20 µL, 10 mg/kg) and X-ray radiation (4 Gy, single fraction). Mice were then maintained for additional 2 weeks. Body weight and tumour volume were measured every other day. After two weeks, mice were sacrificed and tumours were removed, photographed and fixed with 10% neutral-buffered formalin for histological analysis.

Results

Characterization of Liposomes

Figure 2:
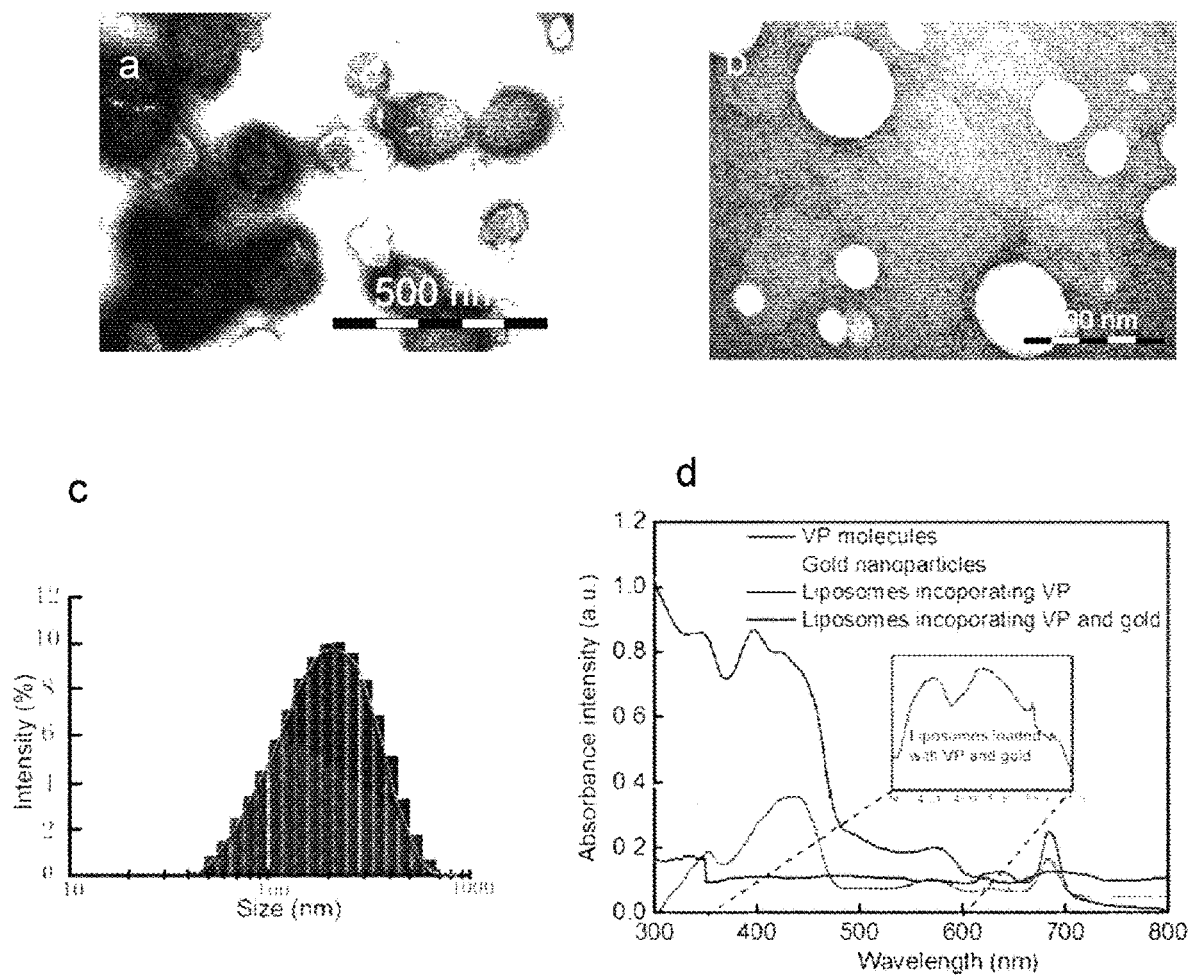
FIG. 2 shows physical and optical properties of liposomes. (a) and (b) Transmission electron microscopy (TEM) images of liposomes containing gold nanoparticles and pure liposomes. (c) Size distribution determined by dynamic light scattering. (d) Absorption spectra of liposomes, pure verteporfin (VP) and pure gold nanoparticles.

FIG. 2(a) illustrates typical TEM images of liposomes containing gold nanoparticles and VP. Gold nanoparticle clusters were easily observed due to the higher electron density of metal gold compared with the lipids. The average size of liposomes was about 165 nm determined by dynamic light scattering and the zeta potential was 37.3±4 mV (FIG. 2(b)). FIG. 2(c) shows the absorption spectra of different liposome samples, where characteristic absorption peaks from both gold nanoparticles and VP were observed. The encapsulation efficiency of oligonucleotide and Dox loaded inside of liposomes was estimated and found to be approximately 37.5% and 44%, respectively.

Singlet Oxygen Generation Tests by Using Two External Stimuli: Light and X-Rays

Figure 3:
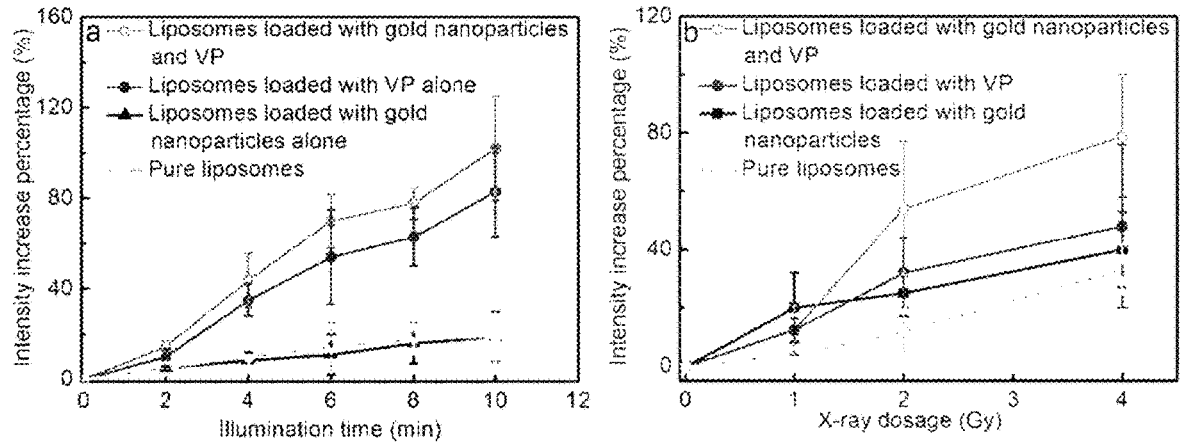
FIG. 3 shows the percentage increase of Singlet Oxygen Sensor Green (SOSG) fluorescence intensities in different liposome samples (a) under 360 nm irradiation at different time points, and (b) X-ray radiation with different doses.

The generation of singlet oxygen is a factor in the oxidation of unsaturated lipids, resulting in the disruption of the liposome structure. $^1O_2$ generation was confirmed by using SOSG and monitoring the enhancement of fluorescence intensity at 488 nm excitation. $^1O_2$ reacts with SOSG to produce endoperoxides which have a strong fluorescence signal at 525 nm for 488 nm excitation, while it has weak fluorescence in the absence of $^1O_2$. It is known that neither gold nanoparticles nor VP molecules are fluorescent at the excitation wavelength of 525 nm. In these circumstances, the measured fluorescence intensity at 525 nm is principally related to the amount of singlet oxygen generated from the VP molecules. The SOSG fluorescence intensity enhancement as a function of light illumination time and X-ray dose respectively is plotted in FIG. 3. FIG. 3(a) shows that the liposomes loaded with gold nanoparticles and VP generate more singlet oxygen than the other samples, with an increase of about 102% after 10 min illumination. Singlet oxygen quantum yield (SOQY) from this sample (liposomes loaded with gold nanoparticles and VP) is calculated to be 0.75±0.18, indicating an enhancement factor of 1.42 compared with the liposomes loaded with VP alone. The details of this calculation are explained below. The enhancement of $^1O_2$ generation from VP is attributed to near-field enhancement of electromagnetic field induced by gold nanoparticles. Similarly, the enhancement of $^1O_2$ generation was observed in liposomes loaded with gold nanoparticles and VP in the X-ray radiation experiments as well but to a lesser extent. As shown in FIG. 3(b), liposomes doped with gold nanoparticles and VP molecules generate the highest amount of $^1O_2$, with a percentage increase of approximately 79% under X-ray radiation with 4 Gy, while liposomes containing gold nanoparticles alone and the sample containing VP alone produced a limited amount of $^1O_2$, with a percentage increase of approximately 48% and 40%, respectively, under the same experimental conditions. The number of singlet oxygen generated from liposomes loaded with VP and gold nanoparticles under X-ray radiation with 4 Gy, was calculated to be 7250 per a single liposome. The calculation is provided below.

The observed enhancement of X-ray induced singlet oxygen generation in the presence of gold nanoparticles can be explained by the following mechanism. Gold is a heavy metal element strongly interacting with X-rays, which leads to a significant increase of the energy deposition in biological tissues when irradiated with such rays. Therefore gold nanoparticles are well known radiosensitizers able to amplify the radiation doses in tumour tissue. In addition, gold nanoparticles can selectively scatter and (or) absorb the high energy X-ray radiation, leading to enhanced energy transfer from X-ray to photosensitizers. With contributions from these mechanisms, the VP molecules in close proximity to gold nanoparticles are able to interact more strongly with ionising radiation than the VP on its own, causing enhanced $^1O_2$ generation.

Calcein Release Assays Under Two External Stimuli

Figure 4:
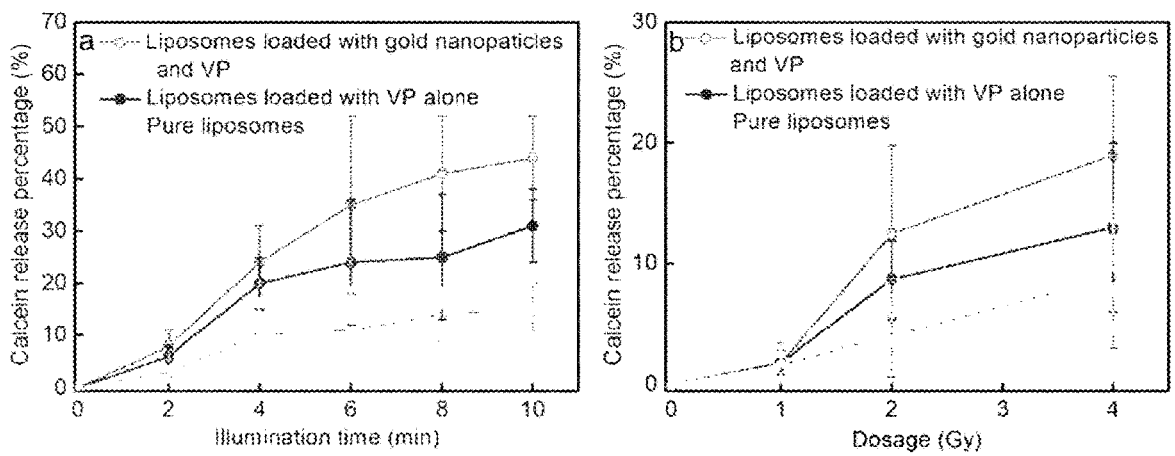
FIG. 4 shows kinetics of calcein release from different liposome samples (a) under 360 nm LED illumination, and (b) X-ray irradiation.

Having confirmed the $^1O_2$ generation from VP entrapped inside liposomes using two stimulating modalities, the liposome content release was evaluated by using a calcein release assay, which is based on the principle of fluorescence self-quenching. FIG. 4 shows the proportion of calcein release from different liposome samples under UV illumination and X-ray exposure, respectively. The amount of calcein released from liposomes doped with both gold nanoparticles and VP reaches a maximum of 44% after 10 min light illumination (FIG. 4(a)) and 19% after X-ray radiation with 4 Gy (FIG. 4(b)), respectively. However, lower leakage is observed in the controls (liposomes doped with VP alone), with only 31% and 13% of calcein being released at the same experimental conditions. Similarly to these results of the $^1O_2$ generation, the findings show that introduction of gold nanoparticles inside liposomes contributes to increased release of entrapped calcein, compared with samples containing VP molecules only, under both UV illumination and X-ray radiation.

Cellular Uptake of Liposome Nanoparticles

Figure 12:
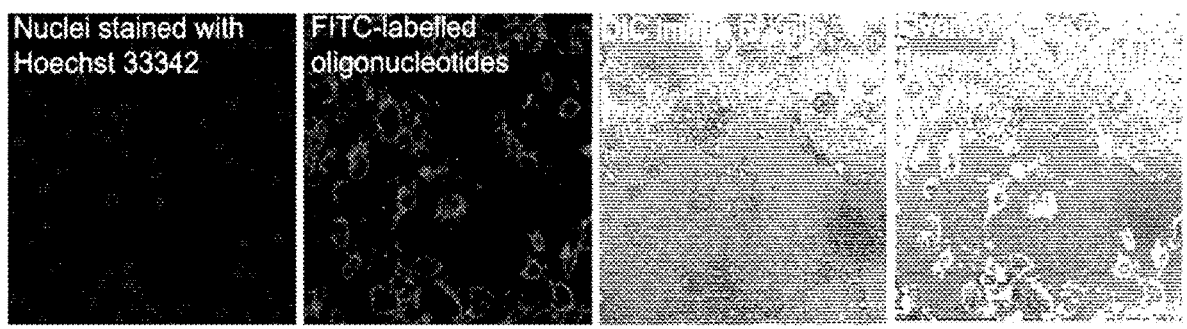
FIG. 12 shows confocal laser scanning microscopy images of PC12 cells incubated with liposome nanoparticles (25 μM) loaded with fluorescent oligonucleotides. Scale bar is 75 μm.

In order to investigate the cellular uptake of liposomes, the PC12 cells were treated with liposomes for 1 h, 4 h and 10 h. Higher red fluorescence signal from VP was observed after 4-h incubation compared with cells treated for 1 h. Detailed characterisation of the cellular uptake of liposomes after 4-h incubation with PC12 cells was determined. In addition, green fluorescence from FAM-labelled oligonucleotide is also clearly observed after 4-h incubation (FIG. 12). After 10-h incubation with liposomes, cells were surrounded by large red clusters, indicating a large amount of liposomes loaded with VP were internalized by cells. However, some clusters were also observed in other regions due to non-specific binding. Therefore, 4-h incubation time was chosen in this study. Based on the concentration of fluorescent lipid internalised by cells, it was estimated that 2550±89 liposomes were internalised by each HCT116 cell. The number of gold nanoparticles per liposome is estimated to be 156±24 on the basis of the ICP-MS data. Therefore, the number of gold nanoparticles internalised by each HCT116 cell is estimated to be 3.98×10$^5$ in this study. The detailed calculation of the number of liposome per cell and the number of gold nanoparticles per liposome is provided below.

Cellular Uptake Activity of Folate-Conjugated Liposomes

The folate receptor (FR) is significantly expressed in many types of cancer cells while its expression in most normal tissues is generally low. Folic acid (FA) has a very high affinity for FR with a minimal effect on its binding ability even after conjugation with other nanomaterials. Therefore FA can significantly enhance the capability of nanoparticle-based delivery systems to target cancer cells. In this study, we modified the liposome surface with folate and determined the average number of the folate molecules per liposome based on the total amount of folate and liposomes in the sample, which is estimated to be approximately 480. To evaluate targeting specificity of the folate-targeted liposomes to tumour cells, the uptake activity of liposomes by colorectal cancer HCT116 cells, was compared to the uptake by normal human colonic epithelium CCD 841 cells. Cancer cells treated with folate-conjugated liposome nanoparticles clearly exhibited red signal from VP in the cytoplasm after 1 h incubation. By contrast, the level of liposome uptake by CCD 841 CoN cells was shown fairly low under the same experimental conditions. These results indicated that FA induced the specific binding to the folate receptor expressed on HCT116 cell surface, resulting in a much higher internalization rate of targeted liposomes, compared to the normal CCD 841 cells.

Singlet Oxygen Quantum Yield Determination from Liposomes Loaded with VP and Gold Nanoparticles after Illumination at 365 nm Wavelength The singlet oxygen quantum yield (φ) is the ratio of the number of photons absorbed by a photosensitizer (PS) molecule to the number of singlet oxygen generated. The reference method is the most commonly used approach for calculating φ (Lin, H. et al 2013). The singlet oxygen quantum yield of a PS ($\varphi_{PS}$) can be calculated based on a reference PS with a known quantum yield ($\varphi_{REF}$) using the equation (Clement et al, 2016a):

$$\varphi_{PS} = \varphi_{REF} \frac{\frac{r_{PS}}{(1-T_{PS})}}{\frac{r_{REF}}{(1-T_{REF})}} \tag{1}$$

where $r_{PS}$ and $r_{REF}$ are the reaction rates of the fluorescent detection probe with singlet oxygen generated from PS and reference PS respectively. $T_{PS}$ and $T_{REF}$ represent the transmittance of the PS and the reference PS at the illumination wavelength.

Figure 8:
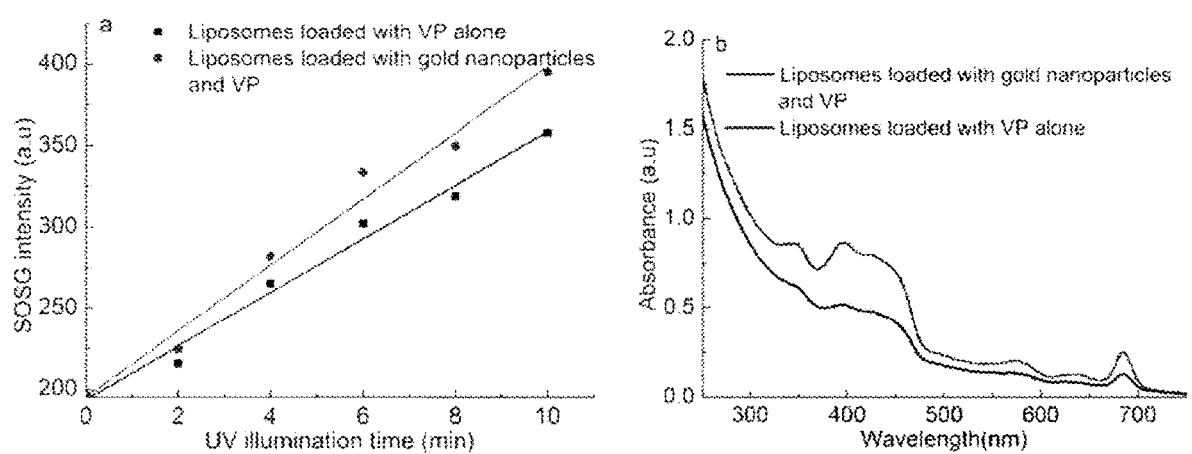
FIG. 8 shows quantification of $^1O_2$ generation under UV illumination for liposomes loaded with VP and gold nanoparticles and liposomes loaded with VP alone. (a) SOSG intensity as a function of UV illumination time. (b) Absorption spectra of these samples.

In this case, the singlet oxygen quantum yield φ of liposomes loaded with VP and gold nanoparticles was determined at 365 nm by taking φ of VP alone as the reference PS (0.53±0.06). FIG. 8(a) shows the variation of SOSG intensity at 525 nm as a function of UV illumination time for liposomes loaded VP alone and liposomes loaded with VP and gold nanoparticles. Their absorption spectra of these nanocomposites are shown in FIG. 8(b). The transmittance value at 365 nm is calculated from absorbance of VP alone and liposomes loaded with VP and gold nanoparticles based on their absorption spectra. Using the equation (1) with the reaction rate and absorbance value obtained from FIG. 8, the singlet oxygen quantum yield φ of liposomes loaded with VP and gold nanoparticles obtained in this work was estimated as 0.75±0.18. This result shows that there is an enhancement in the quantum yield value of liposomes loaded with VP and gold nanoparticles by a factor of 1.42 compared with liposomes loaded with VP alone. This enhancement is tentatively attributed to the electric field enhancement around the gold nanoparticles present in gold-loaded liposomes.

Quantification of Singlet Oxygen from Liposomes Loaded with VP and Gold Nanoparticles Under X-Ray Radiation To quantify the number of singlet oxygen generated from liposomes loaded with VP and gold nanopaticles under X-ray radiation for a particular dose, a relation between the number of singlet oxygen molecules generated by X-ray radiation was established and the intensity of SOSG fluorescence, in a way similar to a previous publication (Clement et al, 2016b).

Figure 9:
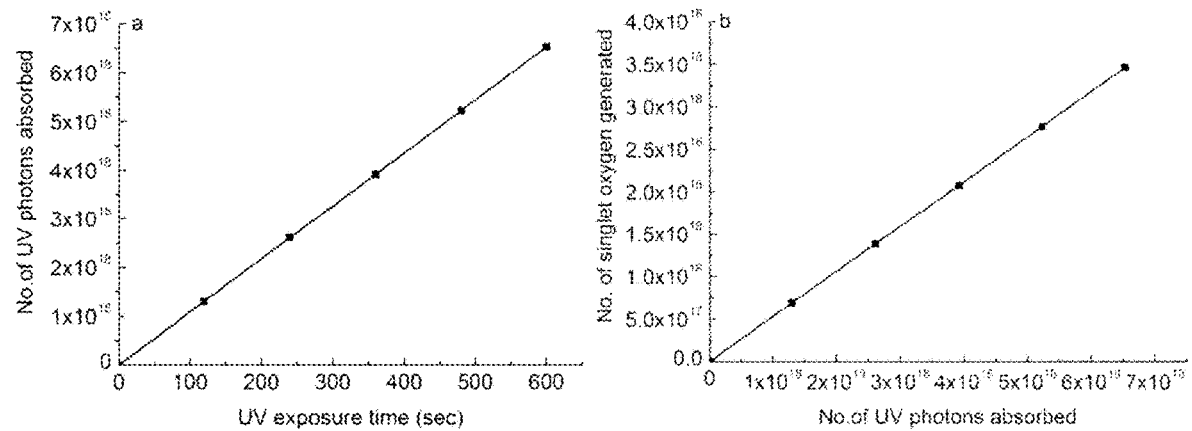
FIG. 9 (a) shows number of UV photons absorbed by liposomes loaded with VP alone as a function of time; (b) Number of singlet oxygen generated versus number of UV photons absorbed.

The number of UV photons absorbed ($N_{uv}(t)$) by liposomes loaded with VP alone was first calculated as a function of time using the equation:

$$N_{uv}(t) = \frac{P}{E} * F * t \qquad (2)$$

where P is the optical power detected on the surface of the sample, E is the energy of 365 nm photons and t is the time of illumination. F is the absorption factor and is calculated from the absorption spectra of the sample. This $N_{uv}(t)$ is plotted against time as shown in FIG. 9(a). From the known singlet oxygen quantum yield φ of VP mentioned above and $N_{uv}(t)$ from FIG. 9(a), the number of singlet oxygen generated corresponding to each UV photons absorbed was calculated. If this number is compared with the SOSG intensity in FIG. 8(a), a conversion factor is obtained which gives the calibration of the SOSG signal with respect to the number of singlet oxygen generated.

Figure 10:
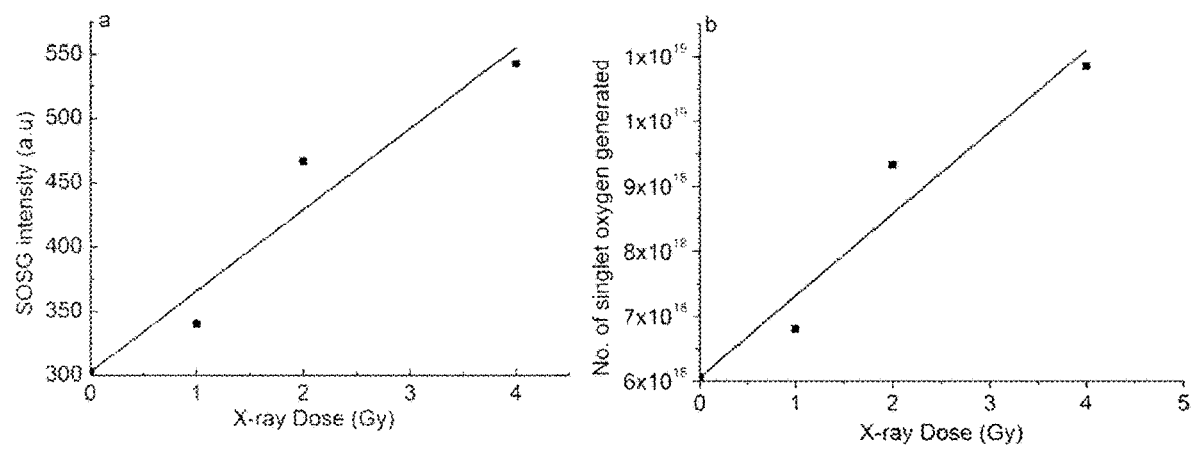
FIG. 10 (a) shows SOSG intensity as a function of X-ray Dose for liposomes loaded with VP and gold nanoparticles; (b) Number of singlet oxygen generated corresponding to each X-ray.

FIG. 10(a) shows the SOSG intensity as a function of X-ray dose applied to liposomes loaded with VP and gold nanoparticles. By using the conversion factor estimated above, the number of singlet oxygen generated corresponding to each X-ray dose was calculated. In this case, the number of singlet oxygen generated from liposomes loaded with VP and gold nanoparticles for 4 Gy is ~2.9×10$^{18}$. By dividing the number of liposomes in this sample, the number of singlet oxygen generated from each liposome, which estimated to be about 7250. In this case, the fact that SOSG shows some background fluorescence due to the presence of endoperoxides generated before the exposure to X-ray radiation was taken into account.

Calculation of the Number of Liposomes Per Cell

The number of lipid molecules in each liposome was first calculated as per the equation (Güven et al 2009):

$$N_{tot} = \frac{\left[4\pi\left(\frac{d}{2}\right)^2 + 4\pi\left[\frac{d}{2} - h\right]^2\right]}{a} \qquad (3)$$

where d is the diameter of a liposome, h indicates the thickness of a liposomal bilayer that was calculated as 4.7 nm for the lipid formulation (Small, 1984), and a represents the average lipid head group area, whose value is calculated according to $a = a_1 N_1 + a_2 N_2 + a_3 N_3 + \ldots$, where N is the molar fraction of each lipid component and a is 70 Å for DOTAP (Koltover et al 1999) and 72.4 Å for DOPC (Kučerka et al 2006) in the present study.

The number of liposome for a known concentration of lipids is estimated by using the equation:

$$N_{lipo} = \frac{[\text{lipid}] \times N_A}{N_{tot} \times 1000} \qquad (4)$$

where [lipid] is the lipid concentration, $N_A$ is the Avogadro number (6.023×10$^{23}$ mol/L) and $N_{tot}$ is the total number of lipids per liposome.

The number of liposome per cell is obtained based on Equation (3) and (4).

Estimation of the Number of Gold Nanoparticles Per Liposome

The total number of gold atom ($N_{atom}$) in the liposome sample was calculated based on ICP-MS analysis and the equation:

$$N_{atom} = \frac{[\text{Au}^{3+}] \times V}{M} \times N_A \qquad (5)$$

where [Au$^{3+}$] is the concentration of Au (III), V stands for the sample volume, M indicates the atomic weight of gold and $N_A$ is the Avogadro number (6.023×10$^{23}$ mol/L).

The average number of gold atoms per gold nanoparticle (U) is also calculated by using the following equation (Chithrani et al, 2006):

$$U = \frac{2}{3} \times \pi \times \left(\frac{D}{\alpha}\right)^3 \qquad (6)$$

Where D refers to the diameter of gold nanoparticle and a is the edge of a unit cell whose value was 4.0786 Å. Therefore the number of gold nanoparticles ($N_{gold}$) in a liposome sample is calculated based on the equation:

$$N_{gold} = \frac{N_{atom}}{U} \qquad (7)$$

Finally the number of gold nanoparticles per liposome (N) is estimated as per the equation:

$$N = \frac{N_{gold}}{N_{lipo}} \quad (8)$$

Serum and pH Stability Studies of PEGylated Liposomes

Figure 11:
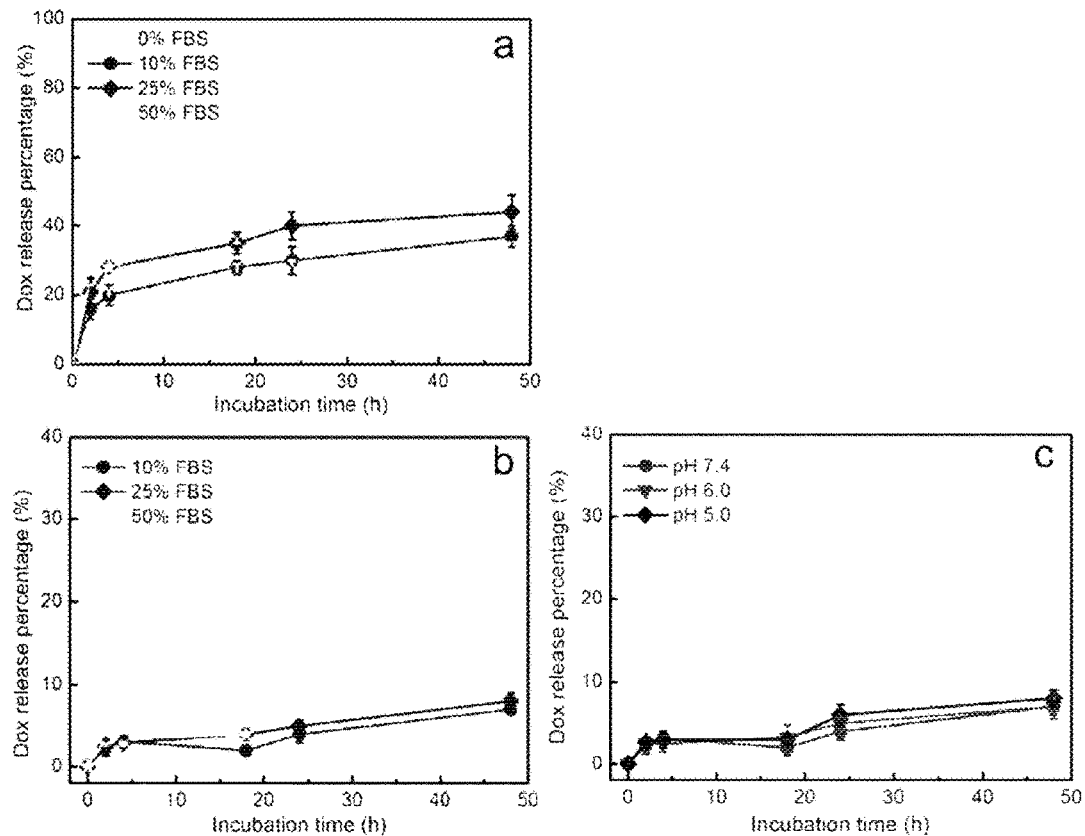
FIG. 11 shows the percentage of released Dox from (a) conventional liposomes and (b) PEGylated liposomes after 0 h, 2 h, 4 h, 18 h, 24 h and 48 h incubation in PBS (pH 7.4) containing FBS with various concentrations. (c) The percentage of released Dox from PEGylated liposome samples incubated in PBS (pH 7.4, 6.0 and 5.0) containing 10% FBS.

For serum stability studies, the cumulative percentage of Dox released from liposomes with and without PEG modification is shown in FIGS. 11(a) and 11(b). Different amounts of Dox were released from conventional liposomes during 48 hr incubation, with the total amount being more than 30% and 50% at 48 hr when incubated in PBS with 10% and 50% FBS (FIG. 11(a)). However the Dox release profile shown in FIG. 11(b) showed that the release rates were largely reduced in the PEGylated liposomes, compared with liposomes without PEGylation. Liposomes still retained more than 90% and 80% of their initial drug content at 48 hr incubated in PBS with 10% and 50% FBS, indicating that PEG chains on the liposome surface would contribute to improved its stability in the blood circulation. Considering that the decreased pH is a major feature of tumour tissue and it would probably affect drug release from liposomes, we also assessed Dox release triggered by pH with different values. These PEGylated liposomes showed a similar Dox release profile at different buffer pH values (7.4, 6.0 and 5.0). The overall amount of released Dox was less than 10% for 48 hr incubation even at pH 5.0 (FIG. 11(c)). These findings suggested that liposome formulation prepared in this study was not largely affected by the decreased pH value, maximising the stability of liposomes in the tumour microenvironment before application of light or X-ray to a tumour site.

X-Ray Triggered In Vitro Gene Silencing and Chemotherapy

PAC1R Gene Silencing Under X-Ray Radiation

Figure 5:
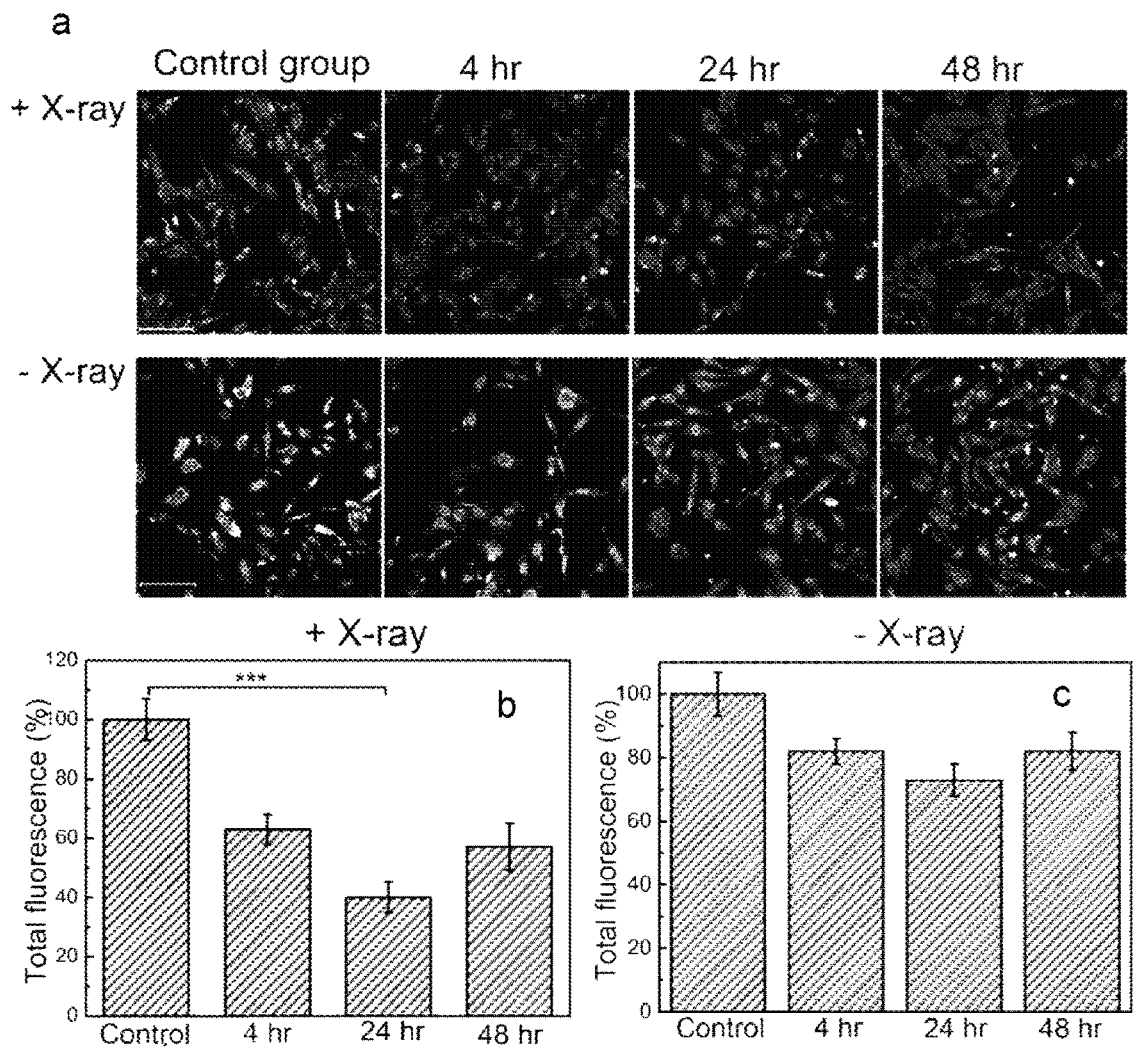
FIG. 5 (a) shows representative confocal images of indirect immunofluorescence staining of PAC1R at different time points after treatment. (a) Top panel: cells treated with X-ray and liposomes. (a) Bottom panel: cells treated with liposomes alone. Quantitative assessment of PAC1R gene silencing induced by antisense oligonucleotide released from liposomes at different time points with (b) and without X-ray radiation (c). Decreased PAC1R was expressed as percentage of the control. The concentration of liposomes incubated with cells was 25 μM. Scale bar was 75 μm.

Liposomes were loaded with antisense oligonucleotide to carry out the PAC1R gene knockdown by delivering the liposomes to PC12 cells and applying 4 Gy of X-ray radiation. The remaining PAC1R fluorescence at various time points was visualized using confocal microscopy. For comparison, the cells treated with liposomes alone, but without triggering were also imaged using the same imaging conditions. As shown in FIG. 5(a), decreased fluorescence in cell samples was clearly observed 24 h after X-ray exposure, indicating that the antisense oligonucleotide released from liposomes effectively knocked down the PAC1R gene expression. For cells treated with liposomes alone, a decreased PAC1R fluorescence signal was also observed at 24 hr after treatment, but the decrease was less pronounced compared to cells treated with X-ray radiation. The PAC1R inhibition at different time points were quantitatively analysed based on cellular fluorescence images. At 4 hr after treatment, a 20% decrease of PAC1R level was observed in cells with X-ray treatment, while almost no change in the level of PAC1R was observed at the same time point in cells treated with liposomes but with the omission of X-ray radiation. After 24 hr since X-ray exposure the density of PAC1R decreased by about 45%, while the level of PAC1R in cells which were not exposed to X-rays but received the liposomes with antisense oligonucleotides decreased by only 30% (FIG. 5(b) and FIG. 5(c)).

Cytotoxicity of LipoDox in HCT116 Cells after X-Ray Radiation

Figure 6:
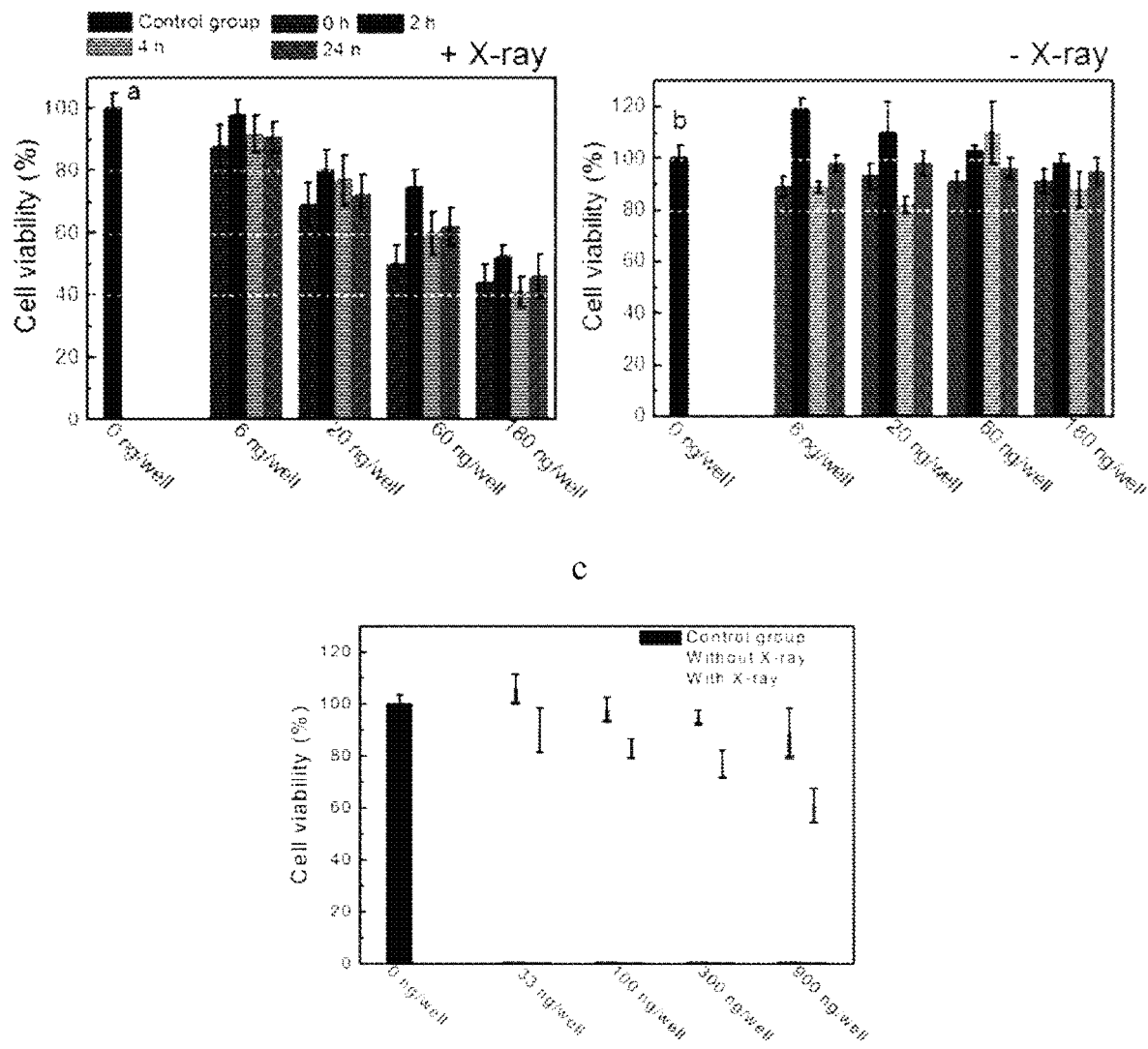
FIG. 6 shows cell-killing effect of LipoDox on HCT116 with (a) and without (b) X-ray radiation of 4 Gy at various time points (0 h, 2 h, 4 h and 24 h). Cells were cultured in 96-well plates. The concentration of Dox was 6, 20, 60 and 160 ng per well. The viabilities are expressed as mean percentages and standard deviation (n=4) relative to control cells. (c) shows cell-killing effect of LipoETP on HCT116 at 24 hours after X-ray radiation of 4 Gy. The concentration of ETP was 33, 100, 300 and 900 ng per well. The viabilities are expressed as mean percentages and standard deviation (n=4) relative to control cells.

In addition to the demonstration of gene silencing by using X-ray triggered liposomes, the in vitro cell-killing effect of similar liposomes loaded with varying amounts of Dox in HCT116 cells was also investigated. A series of drug-dilution assays presented in FIG. 6 reveals that 50% cell-killing ($IC_{50}$) was achieved at 1.6 μM of Dox encapsulated in the liposomes and triggered by X-ray radiation. However, the LipoDox alone, without X-ray triggering but with same Dox concentration of 1.6 μM killed only about 10% of cancer cells. This illustrates, not unexpectedly, that the efficacy of LipoDox for cell killing was higher with X-ray radiation, compared with LipoDox only. The MTS assays did not reveal any significant change of cell viability at 0 h, 4 h and 24 h after X-ray treatment, while an increase of cell viability was observed at 2 h after treatment. The results of the X-ray triggered LipoDox treatment described here indicates that a combination of X-ray triggered chemo- and radiotherapy with the same X-rays appears to produce a synergic effect and it yields improved efficacy of cancer cell-killing. It should be mentioned that both chemo- and radiotherapy would probably contribute to the development of cardiotoxicity, whose incidence was associated with different factors, including the type of antitumour drugs. Therefore we evaluated the cell-killing effect of another chemotherapy drug, ETP, in combination with X-ray radiation. ETP caused relatively less incidence of cardiotoxicity, compared with Dox. As shown in FIG. 6c, higher cytotoxicity of LipoETP in HCT116 cells was observed at 24 hours after X-ray radiation of 4 Gy, compared with LipoETP alone.

Toxicity Assays of Liposome Nanoparticles, LipoDox and X-Ray Exposure

Figure 7:
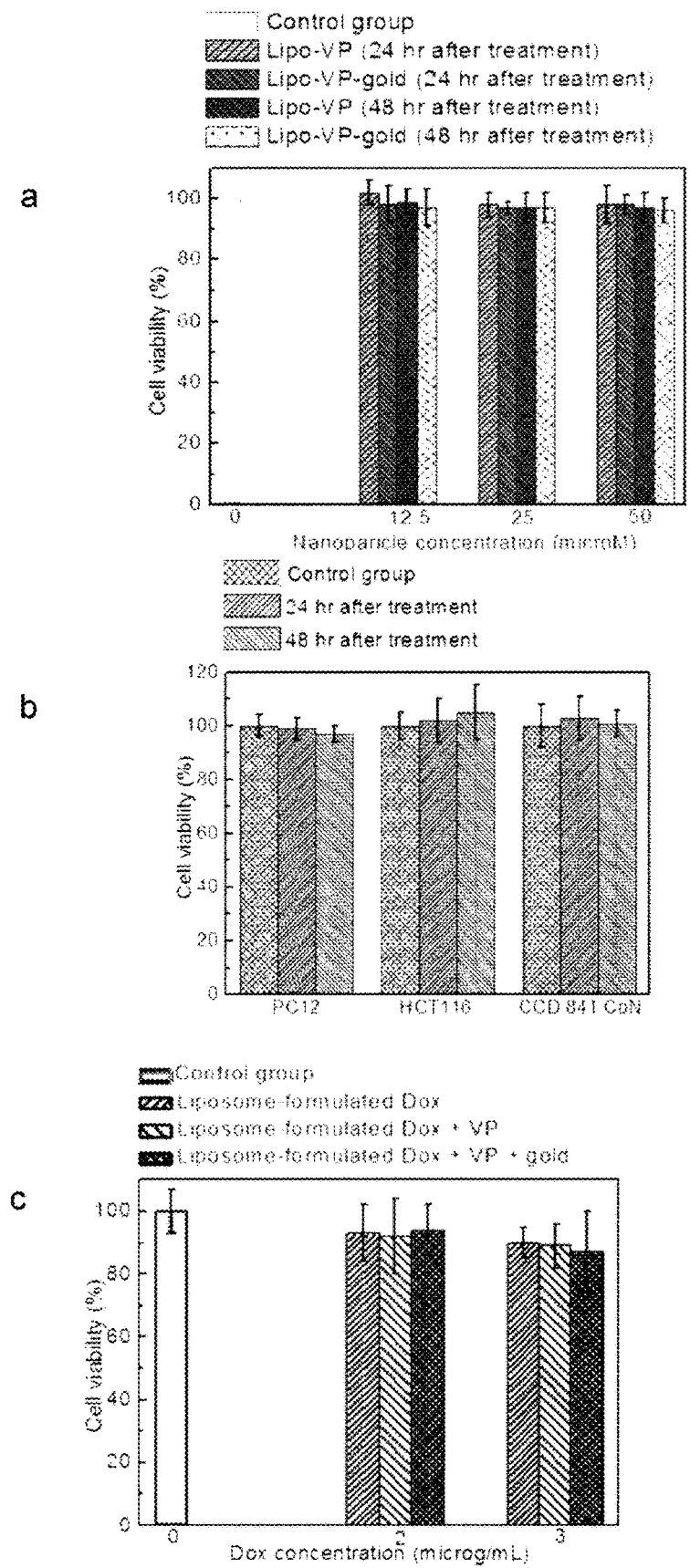
FIG. 7 (a) shows in vitro toxicity assays of liposomes loaded with VP (Lipo-VP) and gold nanoparticles (Lipo-VP-gold) on PC12 cells at 24 hr and 48 hr after incubation. (b) Toxicity of X-ray of 4 Gy on PC12, HCT116 and CCD 841 CoN cells at 24 hr and 48 hr after treatment. (c) Toxicity of liposome-formulated Dox on CCD 841 CoN cells at 24 hr after incubation. Viabilities are expressed as mean percentages and standard deviation (n=4) relative to control cells. (d) Agarose gel electrophoreses of antisense oligonucleotide (10 μg/mL) and mixture of oligonucleotide and VP (10 μg/mL oligonucleotide and 32 μg/mL verteporfin) after X-ray exposure with different dosage. From left to right lane: control sample without treatment, 1 Gy, 2 Gy and 4 Gy.
Figure 7:
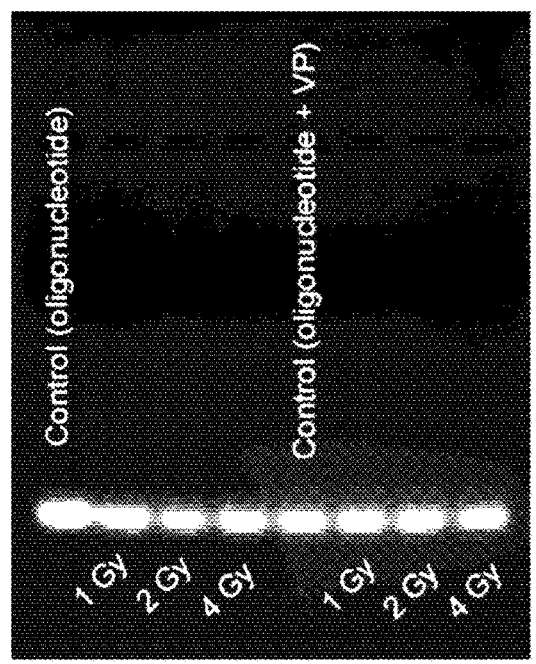

The toxicity of liposomes doped with gold nanoparticles and VP was assessed. Compared with the control group, no significant change was observed in the viability of PC12 cells treated with liposome concentrations up to 50 μM, higher than those used for gene and drug delivery in our study (FIG. 7(a)). The liposome-formulated Dox designed in this study should also have minimal toxicity effect on normal cells without X-ray triggering. To verify this, we examined the toxicity of LipoDox on CCD 841 CoN cells by varying Dox concentration. As shown in FIG. 7(b), we did not observe a noticeable reduction in cell survival (up to 14% cell death) at 24 hr after incubation with liposome-formulated Dox samples (Dox concentration: 3 μg/ml and 2 μg/ml), suggesting that under in vitro conditions, our LipoDox samples with these two Dox concentrations are likely not to affect the viability of CCD 841 CoN cells.

It's well known that radiolysis of water molecules as a result of X-ray radiation would damage DNA molecules by producing toxic radicals. Although cells repair most of the damage, they sometimes leave small areas of misrepair, resulting DNA mutation and may contributing to health problems including cancers. Keeping in mind that X-ray radiation has potential side effects on genetic materials and cells, we particularly check the cytotoxicity of X-ray on gene and cell's viability by irradiating oligonucleotides and cells with X-rays at different dosage.

For cell experiments, the MTS test did not reveal a clear decrease in survival of PC12 cells, HCT116 cells and CCD 841 CoN cells at 24 hr and 48 hr after X-ray exposure (FIG. 7(c)). With regard to the X-ray effect on gene, the DNA gel electrophoresis did not show obvious dispersion of DNA bands after X-ray radiation compared to the control, indicating that X-ray radiation with such dosage did not cause obvious damage to the DNA molecules (FIG. 7(d)).

In addition, the inventors also checked the effect of the singlet oxygen on genetic materials by irradiating mixture solution of oligonucleotides and VP with X-ray. As shown in FIG. 7(d), there was no clear oligonucleotide damage observed compared with the control. Singlet oxygen is the primary cytotoxic agent responsible for photobiological activity involved in the PDT technique. It can damage cells by reacting with many biomolecules, including amino acids, nucleic acids and unsaturated fatty acids that have double bonds as well as sulphur-containing amino acids. Fortunately, the short lifetime of singlet oxygen prevents it from travelling larger distances, therefore it mainly causes damage localised at the photosensitizer where it is generated. In this study singlet oxygen generated from VP loaded in a lipid bilayer would mainly destabilise the unsaturated lipid and consequently induce the drug/gene release. In addition, the lifetime of singlet oxygen will be also significantly reduced following the reaction with lipids. Therefore, the adverse effect of singlet oxygen on oligonucleotides will be significantly minimised.

Evaluation on Therapeutic Effect of X-Ray Triggered Liposomes In Vivo

Figure 13:
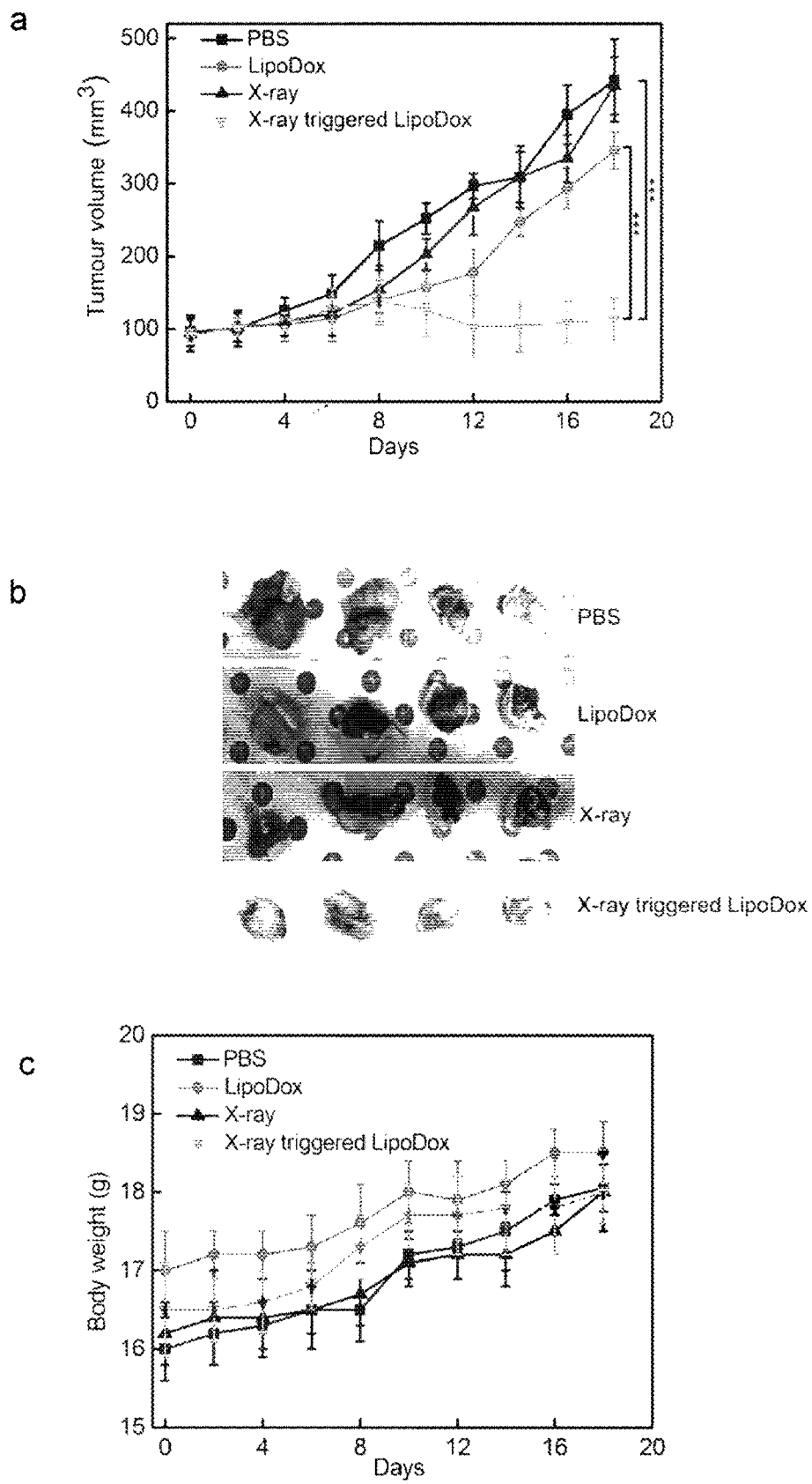
FIG. 13 shows antitumour activity of X-ray triggered LipoDox in a xenograft model of colorectal cancer. (a and c) Changes of tumours and body weight of mice after various treatments indicated. A black arrow indicated the time of treatment administration. The mean tumour volumes were analysed using t test. *P<0.05, P<0.01, *P<0.001. (b) Photographs of tumours isolated at the endpoint.

To determine the efficacy of X-ray triggered liposomes in vivo, we detected their ability to control tumour growth in a xenograft mouse model bearing HCT 1116 cells. The sizes of tumours on mice treated with different conditions were represented in FIG. 13(a). PBS-treated, liposome-treated and X-ray-treated tumour respectively increased 3.0-fold, 2.9-fold and 3.4-fold during the whole period (two weeks post treatment), indicating that these treatments failed to delay tumour progression. By contrast, in the group treated with X-ray triggered liposomes the tumour sizes gradually shrunk at the same time course, with 74% reduction in tumour volume compared to the PBS control group. The size of tumours on mice after different treatments were also photographed and represented in FIG. 13(b), mice treated with X-ray triggered liposomes grew more slowly in comparison with PBS control, X-ray radiation alone and liposome alone. These findings indicated that combined treatment can significantly supress the tumour growth, achieving a better therapeutic outcome, compared with other single treatments. In addition, no mortality was observed during 14 days after treatment with X-ray triggered liposomes, and no weight loss of treated mice was observed compared to the control, suggesting that this combined technique was nontoxic to the mice under the present conditions (FIG. 13(c)).

DISCUSSION

X-ray radiation, as a new external liposome triggering modality, was employed to activate a liposomal gene/drug delivery system in this study. The X-ray triggerable liposomes were designed by encapsulating a photosensitizer, VP and gold nanoparticles in a liposomal bilayer. When these liposomes were exposed to X-rays, enhanced $^1O_2$ generation from VP was achieved due to the interaction between gold nanoparticles with incident x-rays. This $^1O_2$ oxidizes unsaturated lipids and destabilizes the membrane, allowing the release of entrapped cargos from the liposomes. It was demonstrated that this new release strategy has the capacity for in vitro gene knockdown and enhanced cancer cell-killing efficacy by releasing two kinds of cargos, antisense oligonucleotide against PAC1R gene and an antitumour drug (Dox) upon X-ray radiation. In the in vivo experiments, X-ray triggered liposomes were demonstrated to control the colorectal tumour growth more effectively than other single treatment conditions. Although X-rays and other forms of ionizing radiation clinically used to diagnose and treat some medical conditions are widely believed to contribute to DNA mutations at the cellular level and consequently healthy problems, compared with light, compared with light, X-rays can much more easily penetrate through tissues and the body, activating gene/drug release once the X-ray triggered liposomes reach their target. This feature will open many new opportunities for biomedical research and clinical medicine, from triggered gene therapies and chemotherapy, through to enhanced PDT which currently suffers from limited penetration depth of illumination light (usually in the UV and visible region). Additionally, the strategy described here has been designed to be compatible with future clinical translation. The materials and approaches used in this study, such as VP, lipids, Dox and X-rays, are clinically used in treatment of tumours. Although gold nanoparticles used in this study have not yet been approved by the regulatory agencies, their size is compatible with the requirements of renal clearance. In this way, long-term nanoparticle toxicity is likely to be minimized if not eliminated. Moreover, the ease of conjugation of targeting ligands to liposome surface with appropriate linkers, for example, lipid-polyethylene glycol (PEG), would be an added advantage when applied to the targeted therapy, in particular for tumour treatment.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Nahire, R. et al. pH-triggered echogenicity and contents release from liposomes. *Molecular pharmaceutics* 11, 4059-4068 (2014).

Ferreira, D. d. S., Lopes, S. C. d. A., Franco, M. S. & Oliveira, M. C. pH-sensitive liposomes for drug delivery in cancer treatment. *Therapeutic delivery* 4, 1099-1123 (2013).

Dicheva, B. M. et al. Targeted and heat-triggered doxorubicin delivery to tumors by dual targeted cationic thermosensitive liposomes. *Journal of Controlled Release* 195, 37-48 (2014).

Kono, K. et al. Highly temperature-sensitive liposomes based on a thermosensitive block copolymer for tumor-specific chemotherapy. *Biomaterials* 31, 7096-7105 (2010).

Sarkar, N. R. et al. "Uncorking" of liposomes by matrix metalloproteinase-9. *Chem. Commun.*, 999-1001 (2005).

Arouri, A. et al. Development of a Cell-Based Bioassay for Phospholipase A2-Triggered Liposomal Drug Release. *PloS one* 10 (2015).

Leung, S. J. & Romanowski, M. Light-activated content release from liposomes. *Theranostics* 2, 1020 (2012).

Puri, A. Phototriggerable liposomes: current research and future perspectives. *Pharmaceutics* 6, 1-25 (2013).

Wilson, B. C. & Patterson, M. S. The physics, biophysics and technology of photodynamic therapy. *Physics in medicine and biology* 53, R61 (2008).

Miranda, D. and J. F. Lovell, *Mechanisms of Light-induced Liposome Permeabilization*. Bioengineering & Translational Medicine, 2016.

Balazs, D. A. and W. Godbey, *Liposomes for use in gene delivery*. Journal of drug delivery, 2011, Article ID 326497.

Farhood, H., N. Serbina, and L. Huang, *The role of dioleoyl phosphatidylethanolamine in cationic liposome mediated gene transfer*. Biochimica et Biophysica Acta (BBA)-Biomembranes, 1995. 1235(2): p. 289-295.

Su, X.-Y., et al., Enhancement of radiosensitization by metal-based nanoparticles in cancer radiation therapy. Cancer biology & medicine, 2014. 11(2): p. 86-91.

Clement, S., et al., X-ray induced singlet oxygen generation by nanoparticle-photosensitizer conjugates for photodynamic therapy: determination of singlet oxygen quantum yield. Scientific reports, 2016. 6.

Low, P. S., W. A. Henne, and D. D. Doorneweerd, Discovery and development of folic-acid-based receptor targeting for imaging and therapy of cancer and inflammatory diseases. Accounts of chemical research, 2007. 41(1): p. 120-129.

Gabizon, A., et al., Targeting folate receptor with folate linked to extremities of poly (ethylene glycol)-grafted liposomes: in vitro studies. Bioconjugate chemistry, 1999. 10(2): p. 289-298.

Kularatne, S. A. and P. S. Low, Targeting of nanoparticles: folate receptor. Cancer Nanotechnology: Methods and Protocols, 2010: p. 249-265

Li, X., Ding, L., Xu, Y., Wang, Y. & Ping, Q. Targeted delivery of doxorubicin using stealth liposomes modified with transferrin. *International journal of pharmaceutics* 373, 116-123 (2009).

Lin, H. et al. Feasibility study on quantitative measurements of singlet oxygen generation using singlet oxygen sensor green. *Journal of fluorescence* 23, 41-47 (2013).

Clement, S., Sobhan, M., Deng, W., Camilleri, E. & Goldys, E. M. Nanoparticle-mediated singlet oxygen generation from photosensitizers. *Journal of Photochemistry and Photobiology A: Chemistry* (2016a).

Clement, S., Deng, W., Camilleri, E., Wilson, B. C. & Goldys, E. M. X-ray induced singlet oxygen generation by nanoparticle-photosensitizer conjugates for photodynamic therapy: determination of singlet oxygen quantum yield. *Scientific reports* 6 (2016b).

Güven, A., Ortiz, M., Constanti, M. & O'Sullivan, C. K. Rapid and efficient method for the size separation of homogeneous fluorescein-encapsulating liposomes. *Journal of liposome research* 19, 148-154 (2009).

Small, D. M. Lateral chain packing in lipids and membranes. *Journal of Lipid Research* 25, 1490-1500 (1984).

Koltover, I., Salditt, T. & Safinya, C. Phase diagram, stability, and overcharging of lamellar cationic lipid-DNA self-assembled complexes. *Biophysical Journal* 77, 915-924 (1999).

Kučerka, N., Tristram-Nagle, S. & Nagle, J. F. Structure of fully hydrated fluid phase lipid bilayers with monounsaturated chains. *The Journal of membrane biology* 208, 193-202 (2006).

Chithrani, B. D., Ghazani, A. A. & Chan, W. C. Determining the size and shape dependence of gold nanoparticle uptake into mammalian cells. *Nano letters* 6, 662-668 (2006).

Thomas, C. E., Ehrhardt, A. & Kay, M. A. Progress and problems with the use of viral vectors for gene therapy. *Nature reviews. Genetics* 4, 346 (2003).

Zhang, Y., Satterlee, A. & Huang, L. In vivo gene delivery by nonviral vectors: overcoming hurdles? *Molecular therapy* 20, 1298-1304 (2012).

Luo, D. & Saltzman, W. M. Synthetic DNA delivery systems. *Nat Biotechnol* 18, 33-37 (2000)

Sengupta, S., Tyagi, P., Velpandian, T., Gupta, Y. & Gupta, S. Etoposide encapsulated in positively charged liposomes: pharmacokinetic studies in mice and formulation stability studies. *Pharmacological research* 42, 459-464 (2000)

Ishida, T., Iden, D. L. & Allen, T. M. A combinatorial approach to producing sterically stabilized (Stealth) immunoliposomal drugs. *FEBS letters* 460, 129-133 (1999).

Yoshino, K. et al. Comparative studies of irinotecan-loaded polyethylene glycol-modified liposomes prepared using different PEG-modification methods. *Biochimica et Biophysica Acta (BBA)-Biomembranes* 1818, 2901-2907 (2012).

The invention claimed is:

1. A liposomal system for delivery of an active agent, the system comprising:

a liposome comprising an outer lipid bilayer component;

a destabilizing agent embedded inside the lipid bilayer component, the destabilizing agent capable of forming reactive oxygen species to oxidise unsaturated lipids and destabilise liposomal membranes; and an active agent in the liposome;

wherein the active agent is releasable from the liposome by exposure to high energy electromagnetic radiation; and wherein the destabilizing agent consists of:

a metal nanoparticle selected from the group consisting of gold, silver and bismuth or a cerium fluoride ($CeF_3$) inorganic nanoparticle, and a photosensitizer selected from the group consisting of verteporfin, rose bengal, aminolevulinic acid, and porfimer sodium.

2. The liposomal system according to claim 1 wherein the lipid bilayer component comprises naturally occurring lipids.

3. The liposomal system according to claim 1 wherein the lipid bilayer component comprises 1,2-dioleoyl-sn-glycero-3-phosphocholine (DOPC) and 1, 2-di-(9Z-octadecenoyl)-3-trimethylammonium-propane (DOTAP), or 1,2-dioleoyl-sn-glycero-3-phosphoethanolamine (DOPE) and N-[1-(2,3-dioleyloxy)propyl]-N,N,N-trimethylammonium chloride (DOTMA).

4. The liposomal system according to claim 1 wherein the photosensitizer is verteporfin.

5. The liposomal system according to claim 1 wherein the destabilizing agent is a gold nanoparticle and verteporfin.

6. The liposomal system according to claim 1 wherein the active agent is selected from the group consisting of a chemotherapy agent, a pharmaceutical, a medical imaging agent, an antisense oligonucleotide and a small interfering RNA (siRNA) molecule for gene silencing and therapy, a biologically active agent, an antibody, an antibody fragment, a protein, a peptide, and a nucleic acid.

7. The liposomal system according to claim 6 wherein the active agent is a chemotherapy agent selected from the group consisting of doxorubicin, vincristine, 5-fluorouracil and etoposide phosphate.

8. The liposomal system according to claim 7 wherein the chemotherapy agent is doxorubicin.

9. The liposomal system according to claim 6 wherein the active agent is an antisense oligonucleotide.

10. The liposomal system according to claim 1 further comprising an uptake material to cause uptake of the liposome into a target region or target cell of a subject.

11. The liposomal system according to claim 10 wherein the uptake material is selected from the group consisting of an antigen, an antibody, an antibody fragment, a peptide, a hormone, a cytokine, a ligand, and a receptor.

12. The liposomal system according to claim 1 wherein the high energy electromagnetic radiation has a photon energy of at least about 6 MeV.

13. The liposomal system according to claim 12 wherein the high energy electromagnetic radiation is x-ray radiation or gamma-ray radiation.

14. The liposomal system according to claim 1, wherein the lipid bilayer component comprises one or more selected from the group consisting of phospholipids and cholesterol.

15. A method for administering an active agent to a subject, the method comprising:
   (a) providing a liposomal system to a subject, said liposomal system comprising:
      a liposome comprising an outer lipid bilayer component;
      a destabilizing agent embedded inside the lipid bilayer component, the destabilizing agent capable of forming reactive oxygen species to oxidise unsaturated lipids and destabilise liposomal membranes; and
      an active agent in the liposome;
   wherein the active agent is releasable from the liposome by exposure to high energy electromagnetic radiation, and
   wherein the destabilizing agent consists of:
      a metal nanoparticle selected from the group consisting of gold, silver and bismuth or a cerium fluoride ($CeF_3$) inorganic nanoparticle, and
      a photosensitizer selected from the group consisting of verteporfin, rose bengal, aminolevulinic acid, and porfimer sodium; and
   (b) exposing the subject to high energy electromagnetic radiation to release the active agent from the liposome to treat the subject.

16. The method according to claim 15 wherein the high energy electromagnetic radiation is x-ray radiation or gamma ray radiation.

* * * * *

UNITED STATES PATENT AND TRADEMARK OFFICE
CERTIFICATE OF CORRECTION

PATENT NO. : 12,036,282 B2
APPLICATION NO. : 16/770930
DATED : July 16, 2024
INVENTOR(S) : Goldys et al.

It is certified that error appears in the above-identified patent and that said Letters Patent is hereby corrected as shown below:

On the Title Page

Page 2, Column 2, Line 51, References Cited, OTHER PUBLICATIONS, Garashi, Akira et al. cite: Please correct "Garashi" to read --Igarashi--

In the Specification

Column 2, Lines 65-66: Please delete the paragraph break between "photosensitizer." and "The destabilizing"

Column 12, Line 54: Please correct "C02" to read --$CO_2$--

Column 13, Line 42: Please correct "HCT16" to read --HCT116--

Column 14, Line 29: Please correct "V=π/6xLxW²" to read --$V = \pi/6 \times L \times W^2$--

Column 17, Line 1: Please correct "r$_{PS}$ and r$_{REF}$" to read --$T_{PS}$ and $T_{REF}$--

Column 18, Line 16: Please correct "a" to read --α--

Column 18, Line 18: Please correct "a=a₁N₁+a₂ N₂+a₃ N₃+ . . .," to read --$\alpha = \alpha_1 N_1 + \alpha_2 N_2 + \alpha_3 N_3 +$ . . .,--

Column 18, Line 19: Please correct "a" to read --α--

Column 18, Line 58: Please correct "a" to read --α--

Signed and Sealed this
Tenth Day of September, 2024

*Katherine Kelly Vidal*
Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: FAM labelled

<400> SEQUENCE: 1
tggtgcttcc cagccactat                                                   20
```